United States Patent
Forde et al.

(10) Patent No.: US 8,795,329 B2
(45) Date of Patent: Aug. 5, 2014

(54) REMOVABLE INTRACARDIAC RF DEVICE

(75) Inventors: Sean Forde, Watertown, MA (US);
James Scutti, Arlington, MA (US);
David J. Callaghan, Mansfield, MA (US); Erik Glaser, Waltham, MA (US);
Carol A. Devellian, Topsfield, MA (US);
Steve W Opolski, Carlisle, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 876 days.

(21) Appl. No.: 12/856,654

(22) Filed: Aug. 15, 2010

(65) Prior Publication Data

US 2010/0312236 A1 Dec. 9, 2010

Related U.S. Application Data

(62) Division of application No. 11/516,145, filed on Sep. 6, 2006, now Pat. No. 7,797,056.

(60) Provisional application No. 60/714,332, filed on Sep. 6, 2005.

(51) Int. Cl.
*A61B 17/04* (2006.01)

(52) U.S. Cl.
USPC .......................................................... 606/213

(58) Field of Classification Search
USPC .............................. 607/116; 606/32–52, 213;
623/1.1–1.54, 13.17, 13.18, 23.72
See application file for complete search history.

(56) References Cited

U.S. PATENT DOCUMENTS

| | | |
|---|---|---|
| 3,874,388 A | 4/1975 | King et al. |
| 4,007,743 A | 2/1977 | Blake |
| 4,696,300 A | 9/1987 | Anderson |
| 4,710,192 A | 12/1987 | Liotta et al. |
| 4,836,204 A | 6/1989 | Landymore et al. |
| 4,902,508 A | 2/1990 | Badylak et al. |
| 4,917,089 A | 4/1990 | Sideris |
| 4,921,484 A | 5/1990 | Hillstead |
| 4,944,741 A | 7/1990 | Hasson |
| 4,945,912 A | 8/1990 | Langberg |

(Continued)

FOREIGN PATENT DOCUMENTS

| | | |
|---|---|---|
| EP | 0553259 B1 | 3/1995 |
| EP | 1013227 A2 | 6/2000 |

(Continued)

OTHER PUBLICATIONS

ISR & Written Opinion for International Application Serial No. PCT/US2006/034504, mailed Apr. 23, 2007 (9 pages).

(Continued)

*Primary Examiner* — Scott Getzow
(74) *Attorney, Agent, or Firm* — DLA Piper LLP (US)

(57) ABSTRACT

The present invention provides systems and methods for occluding or closing a patent foramen ovale of a patient (PFO). The invention includes a catheter carrying an energy delivery element. The catheter introduces the energy delivery element into the patent foramen ovale of a patient's heart. Once appropriately positioned, the energy delivery element applies energy, such as radiofrequency energy, to the tissues surrounding the patent foramen ovale. The application of energy causes the tissues to join together, occluding the patent foramen ovale. The energy delivery element may be removable or permanently implanted in the patent foramen ovale.

16 Claims, 20 Drawing Sheets

(56) References Cited

U.S. PATENT DOCUMENTS

| | | |
|---|---|---|
| 4,946,440 A | 8/1990 | Hall |
| 4,956,178 A | 9/1990 | Badylak et al. |
| 4,967,765 A | 11/1990 | Turner et al. |
| 5,003,990 A | 4/1991 | Osypka |
| 5,007,908 A | 4/1991 | Rydell |
| 5,021,059 A | 6/1991 | Kensey et al. |
| 5,025,799 A | 6/1991 | Wilson |
| 5,108,420 A | 4/1992 | Marks |
| 5,156,613 A | 10/1992 | Sawyer |
| 5,171,259 A | 12/1992 | Inoue |
| 5,176,687 A | 1/1993 | Hasson et al. |
| 5,217,435 A | 6/1993 | Kring |
| 5,222,974 A | 6/1993 | Kensey et al. |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,334,217 A | 8/1994 | Das |
| 5,370,644 A | 12/1994 | Langberg |
| 5,385,156 A | 1/1995 | Oliva |
| 5,423,882 A | 6/1995 | Jackman et al. |
| 5,425,744 A | 6/1995 | Fagan et al. |
| 5,433,727 A | 7/1995 | Sideris |
| 5,451,235 A | 9/1995 | Lock et al. |
| 5,484,385 A | 1/1996 | Rishton |
| 5,486,185 A | 1/1996 | Freitas et al. |
| 5,486,193 A | 1/1996 | Bourne et al. |
| 5,507,744 A | 4/1996 | Tay et al. |
| 5,507,811 A | 4/1996 | Koike et al. |
| 5,540,681 A | 7/1996 | Strul et al. |
| 5,573,533 A | 11/1996 | Strul |
| 5,578,045 A | 11/1996 | Das |
| 5,597,378 A | 1/1997 | Jervis |
| 5,620,461 A | 4/1997 | Muijs Van De Moer et al. |
| 5,620,479 A | 4/1997 | Diederich |
| 5,626,599 A | 5/1997 | Bourne et al. |
| 5,630,837 A | 5/1997 | Crowley |
| 5,634,936 A | 6/1997 | Linden et al. |
| 5,636,634 A | 6/1997 | Kordis et al. |
| 5,649,950 A | 7/1997 | Bourne et al. |
| 5,653,684 A | 8/1997 | Laptewicz et al. |
| 5,669,934 A | 9/1997 | Sawyer |
| 5,676,662 A | 10/1997 | Fleischhacker et al. |
| 5,683,411 A | 11/1997 | Kavteladze et al. |
| 5,690,675 A | 11/1997 | Sawyer et al. |
| 5,702,421 A | 12/1997 | Schneidt |
| 5,709,707 A | 1/1998 | Lock et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,249 A | 4/1998 | Moss et al. |
| 5,741,297 A | 4/1998 | Simon |
| 5,749,895 A | 5/1998 | Sawyer et al. |
| 5,797,905 A | 8/1998 | Fleischman et al. |
| 5,797,907 A | 8/1998 | Clement |
| 5,797,960 A | 8/1998 | Stevens et al. |
| 5,800,428 A | 9/1998 | Nelson et al. |
| 5,800,478 A | 9/1998 | Chen et al. |
| 5,807,384 A | 9/1998 | Mueller |
| 5,810,810 A | 9/1998 | Tay et al. |
| 5,810,884 A | 9/1998 | Kim |
| 5,823,956 A | 10/1998 | Roth et al. |
| 5,846,261 A | 12/1998 | Kotula et al. |
| 5,849,028 A | 12/1998 | Chen |
| 5,853,422 A | 12/1998 | Huebsch et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,895,412 A | 4/1999 | Tucker |
| 5,904,703 A | 5/1999 | Gilson |
| 5,919,200 A | 7/1999 | Stambaugh et al. |
| 5,927,284 A | 7/1999 | Borst et al. |
| 5,944,738 A | 8/1999 | Amplatz et al. |
| 5,948,011 A | 9/1999 | Knowlton |
| 5,954,719 A | 9/1999 | Chen et al. |
| 5,955,110 A | 9/1999 | Patel et al. |
| 5,957,919 A | 9/1999 | Laufer |
| 5,964,782 A | 10/1999 | Lafontaine et al. |
| 5,971,980 A | 10/1999 | Sherman |
| 5,976,174 A | 11/1999 | Ruiz |
| 5,993,844 A | 11/1999 | Abraham et al. |
| 5,997,575 A | 12/1999 | Whitson et al. |
| 6,004,316 A | 12/1999 | Laufer |
| 6,010,517 A | 1/2000 | Baccaro |
| 6,015,378 A | 1/2000 | Borst et al. |
| 6,016,811 A | 1/2000 | Knopp et al. |
| 6,024,756 A | 2/2000 | Huebsch et al. |
| 6,063,080 A | 5/2000 | Nelson et al. |
| 6,063,085 A | 5/2000 | Tay et al. |
| 6,077,291 A | 6/2000 | Das |
| 6,080,182 A | 6/2000 | Shaw et al. |
| 6,086,581 A | 7/2000 | Reynolds et al. |
| 6,086,610 A | 7/2000 | Duerig et al. |
| 6,106,520 A | 8/2000 | Laufer et al. |
| 6,106,532 A | 8/2000 | Koike et al. |
| 6,117,159 A | 9/2000 | Huebsch et al. |
| 6,123,718 A | 9/2000 | Tu et al. |
| 6,132,438 A | 10/2000 | Fleischman et al. |
| 6,135,997 A | 10/2000 | Laufer et al. |
| 6,143,037 A | 11/2000 | Goldstein et al. |
| 6,152,144 A | 11/2000 | Lesh et al. |
| 6,152,918 A | 11/2000 | Padilla et al. |
| 6,165,183 A | 12/2000 | Kuehn et al. |
| 6,171,329 B1 | 1/2001 | Shaw et al. |
| 6,174,322 B1 | 1/2001 | Schneidt |
| 6,187,039 B1 | 2/2001 | Hiles et al. |
| 6,200,313 B1 | 3/2001 | Abe et al. |
| 6,206,907 B1 | 3/2001 | Marino et al. |
| 6,212,426 B1 | 4/2001 | Swanson |
| 6,214,029 B1 | 4/2001 | Thill et al. |
| 6,221,092 B1 | 4/2001 | Koike et al. |
| 6,231,516 B1 | 5/2001 | Keilman et al. |
| 6,231,561 B1 | 5/2001 | Frazier et al. |
| 6,238,415 B1 | 5/2001 | Sepetka et al. |
| 6,251,128 B1 | 6/2001 | Knopp et al. |
| 6,270,515 B1 * | 8/2001 | Linden et al. ................ 606/213 |
| 6,283,935 B1 | 9/2001 | Laufer et al. |
| 6,287,317 B1 | 9/2001 | Makower et al. |
| 6,290,674 B1 | 9/2001 | Roue et al. |
| 6,290,699 B1 | 9/2001 | Hall et al. |
| 6,292,700 B1 | 9/2001 | Morrison et al. |
| 6,306,424 B1 | 10/2001 | Vyakarnam et al. |
| 6,312,446 B1 | 11/2001 | Huebsch et al. |
| 6,325,798 B1 | 12/2001 | Edwards et al. |
| 6,328,727 B1 | 12/2001 | Frazier et al. |
| 6,336,926 B1 | 1/2002 | Goble |
| 6,338,726 B1 | 1/2002 | Edwards et al. |
| 6,338,731 B1 | 1/2002 | Laufer et al. |
| 6,352,561 B1 | 3/2002 | Leopold et al. |
| 6,355,052 B1 | 3/2002 | Neuss et al. |
| 6,364,853 B1 | 4/2002 | French et al. |
| 6,364,876 B1 | 4/2002 | Erb et al. |
| 6,364,878 B1 | 4/2002 | Hall |
| 6,368,340 B2 | 4/2002 | Malecki et al. |
| 6,375,671 B1 | 4/2002 | Kobayashi et al. |
| 6,379,368 B1 | 4/2002 | Corcoran et al. |
| 6,398,779 B1 | 6/2002 | Buysse et al. |
| 6,402,772 B1 | 6/2002 | Amplatz et al. |
| 6,419,669 B1 | 7/2002 | Frazier et al. |
| 6,430,446 B1 | 8/2002 | Knowlton |
| 6,432,119 B1 | 8/2002 | Saadat |
| 6,436,088 B2 | 8/2002 | Frazier et al. |
| 6,440,152 B1 | 8/2002 | Gainor et al. |
| 6,458,100 B2 | 10/2002 | Roue et al. |
| 6,461,327 B1 | 10/2002 | Addis et al. |
| 6,488,706 B1 | 12/2002 | Solymar |
| 6,494,881 B1 | 12/2002 | Bales et al. |
| 6,503,247 B2 | 1/2003 | Swartz et al. |
| 6,506,189 B1 | 1/2003 | Rittman, II et al. |
| 6,527,767 B2 | 3/2003 | Wang et al. |
| 6,527,786 B1 | 3/2003 | Davis et al. |

(56) References Cited

U.S. PATENT DOCUMENTS

| | | | |
|---|---|---|---|
| 6,540,742 B1 | 4/2003 | Thomas et al. | |
| 6,544,260 B1 | 4/2003 | Markel et al. | |
| 6,551,303 B1 | 4/2003 | Van Tessel et al. | |
| 6,551,344 B2 | 4/2003 | Thill | |
| 6,558,375 B1 | 5/2003 | Sinofsky et al. | |
| 6,558,385 B1 | 5/2003 | McClurken et al. | |
| 6,582,430 B2 | 6/2003 | Hall | |
| 6,596,013 B2 | 7/2003 | Yang et al. | |
| 6,616,655 B1 | 9/2003 | Falwell et al. | |
| 6,623,508 B2 | 9/2003 | Shaw et al. | |
| 6,626,901 B1 | 9/2003 | Treat et al. | |
| 6,632,223 B1 | 10/2003 | Keane | |
| 6,641,579 B1 | 11/2003 | Bernardi et al. | |
| 6,645,225 B1 * | 11/2003 | Atkinson | 606/213 |
| 6,650,923 B1 | 11/2003 | Lesh et al. | |
| 6,652,517 B1 | 11/2003 | Hall et al. | |
| 6,656,206 B2 | 12/2003 | Corcoran et al. | |
| 6,659,105 B2 | 12/2003 | Burbank et al. | |
| 6,666,861 B1 | 12/2003 | Grabek | |
| 6,666,863 B2 | 12/2003 | Wentzel et al. | |
| 6,673,068 B1 | 1/2004 | Berube | |
| 6,673,090 B2 | 1/2004 | Root et al. | |
| 6,676,656 B2 | 1/2004 | Sinofsky | |
| 6,701,176 B1 | 3/2004 | Halperin et al. | |
| 6,702,835 B2 | 3/2004 | Ginn | |
| 6,709,432 B2 | 3/2004 | Ferek-Patric | |
| 6,712,804 B2 | 3/2004 | Roue et al. | |
| 6,712,815 B2 | 3/2004 | Sampson et al. | |
| 6,712,836 B1 | 3/2004 | Berg et al. | |
| 6,723,092 B2 | 4/2004 | Brown et al. | |
| 6,730,081 B1 | 5/2004 | Desai | |
| 6,735,532 B2 | 5/2004 | Freed et al. | |
| 6,743,184 B2 | 6/2004 | Sampson et al. | |
| 6,743,197 B1 | 6/2004 | Edwards | |
| 6,755,822 B2 | 6/2004 | Reu et al. | |
| 6,764,486 B2 | 7/2004 | Natale | |
| 6,770,070 B1 | 8/2004 | Balbierz | |
| 6,776,780 B2 | 8/2004 | Mulier et al. | |
| 6,780,183 B2 | 8/2004 | Jimenez, Jr. et al. | |
| 6,796,981 B2 | 9/2004 | Wham et al. | |
| 6,802,843 B2 | 10/2004 | Truckai et al. | |
| 6,805,130 B2 | 10/2004 | Tasto et al. | |
| 6,813,520 B2 | 11/2004 | Truckai et al. | |
| 6,821,273 B2 | 11/2004 | Mollenauer | |
| 6,913,579 B2 | 7/2005 | Truckai et al. | |
| 6,939,348 B2 | 9/2005 | Malecki et al. | |
| 7,165,552 B2 | 1/2007 | Deem et al. | |
| 7,901,461 B2 * | 3/2011 | Harmon et al. | 623/23.72 |
| 2001/0014800 A1 | 8/2001 | Frazier et al. | |
| 2001/0034537 A1 | 10/2001 | Shaw et al. | |
| 2001/0037129 A1 | 11/2001 | Thill | |
| 2001/0039435 A1 | 11/2001 | Roue et al. | |
| 2001/0041914 A1 | 11/2001 | Frazier et al. | |
| 2002/0010481 A1 | 1/2002 | Jayaraman | |
| 2002/0026094 A1 | 2/2002 | Roth | |
| 2002/0029048 A1 | 3/2002 | Miller | |
| 2002/0032462 A1 | 3/2002 | Houser et al. | |
| 2002/0035374 A1 | 3/2002 | Borillo et al. | |
| 2002/0052572 A1 | 5/2002 | Franco et al. | |
| 2002/0096183 A1 | 7/2002 | Stevens et al. | |
| 2002/0111645 A1 | 8/2002 | Wang et al. | |
| 2002/0111647 A1 | 8/2002 | Khairkhahan et al. | |
| 2002/0129819 A1 | 9/2002 | Feldman et al. | |
| 2002/0183786 A1 | 12/2002 | Girton | |
| 2002/0183787 A1 | 12/2002 | Wahr et al. | |
| 2003/0028213 A1 | 2/2003 | Thill et al. | |
| 2003/0045893 A1 | 3/2003 | Ginn | |
| 2003/0045901 A1 | 3/2003 | Opolski | |
| 2003/0050665 A1 | 3/2003 | Ginn | |
| 2003/0073979 A1 | 4/2003 | Naimark et al. | |
| 2003/0088242 A1 | 5/2003 | Prakash et al. | |
| 2003/0100920 A1 | 5/2003 | Akin et al. | |
| 2003/0139819 A1 | 7/2003 | Beer et al. | |
| 2003/0144694 A1 | 7/2003 | Chanduszko et al. | |
| 2003/0181945 A1 | 9/2003 | Opolski et al. | |
| 2003/0191495 A1 | 10/2003 | Ryan et al. | |
| 2003/0191526 A1 | 10/2003 | Van Tassel et al. | |
| 2003/0195530 A1 | 10/2003 | Thill | |
| 2003/0195531 A1 | 10/2003 | Gardiner et al. | |
| 2003/0204203 A1 | 10/2003 | Khairkhahan et al. | |
| 2003/0208232 A1 | 11/2003 | Blaeser et al. | |
| 2004/0044361 A1 | 3/2004 | Frazier et al. | |
| 2004/0092973 A1 | 5/2004 | Chanduszko et al. | |
| 2004/0143277 A1 | 7/2004 | Marino et al. | |
| 2004/0143291 A1 | 7/2004 | Corcoran et al. | |
| 2004/0143293 A1 | 7/2004 | Marino et al. | |
| 2004/0143294 A1 | 7/2004 | Corcoran et al. | |
| 2004/0193147 A1 | 9/2004 | Malecki et al. | |
| 2004/0220596 A1 | 11/2004 | Frazier et al. | |
| 2004/0220610 A1 | 11/2004 | Kreidler et al. | |
| 2004/0230185 A1 | 11/2004 | Malecki et al. | |
| 2004/0243122 A1 | 12/2004 | Auth et al. | |
| 2004/0254572 A1 | 12/2004 | McIntyre et al. | |
| 2004/0267191 A1 | 12/2004 | Gifford et al. | |
| 2004/0267306 A1 | 12/2004 | Blaeser et al. | |
| 2005/0021016 A1 | 1/2005 | Malecki et al. | |
| 2005/0034735 A1 | 2/2005 | Deem et al. | |
| 2005/0070887 A1 | 3/2005 | Taimisto et al. | |
| 2005/0080406 A1 | 4/2005 | Malecki et al. | |
| 2005/0125032 A1 | 6/2005 | Whisenant et al. | |
| 2005/0131401 A1 | 6/2005 | Malecki et al. | |
| 2005/0131460 A1 | 6/2005 | Gifford, III et al. | |
| 2006/0027241 A1 | 2/2006 | Malecki et al. | |
| 2006/0074410 A1 | 4/2006 | Malecki et al. | |
| 2006/0241581 A1 | 10/2006 | Malecki et al. | |
| 2006/0241582 A1 | 10/2006 | Malecki et al. | |
| 2006/0241583 A1 | 10/2006 | Malecki et al. | |
| 2006/0241584 A1 | 10/2006 | Malecki et al. | |
| 2006/0247612 A1 | 11/2006 | Malecki et al. | |
| 2006/0271030 A1 | 11/2006 | Francis et al. | |
| 2006/0271040 A1 | 11/2006 | Horne et al. | |
| 2006/0271089 A1 | 11/2006 | Alejandro et al. | |
| 2006/0276779 A1 | 12/2006 | Malecki et al. | |
| 2006/0276846 A1 | 12/2006 | Malecki et al. | |
| 2007/0010806 A1 | 1/2007 | Malecki et al. | |
| 2007/0044811 A1 | 3/2007 | Deem et al. | |

FOREIGN PATENT DOCUMENTS

| | | |
|---|---|---|
| EP | 1046375 A1 | 10/2000 |
| EP | 1222897 A2 | 7/2002 |
| EP | 0750905 B1 | 1/2003 |
| GB | 2407985 A | 5/2005 |
| WO | WO 95/13111 | 5/1995 |
| WO | WO 96/25179 | 8/1996 |
| WO | WO 96/29946 | 10/1996 |
| WO | WO 96/31157 | 10/1996 |
| WO | WO 97/28744 | 8/1997 |
| WO | WO 98/39063 | 9/1998 |
| WO | WO 99/05977 | 2/1999 |
| WO | WO 99/18862 | 4/1999 |
| WO | WO 99/18864 | 4/1999 |
| WO | WO 99/18870 | 4/1999 |
| WO | WO 99/18871 | 4/1999 |
| WO | WO 00/18331 | 4/2000 |
| WO | WO 0/27292 | 5/2000 |
| WO | WO 00/74555 | 12/2000 |
| WO | WO 01/21247 | 3/2001 |
| WO | WO 01/30266 | 5/2001 |
| WO | WO 01/30267 | 5/2001 |
| WO | WO 01/30268 | 5/2001 |
| WO | WO 01/49185 | 7/2001 |
| WO | WO 02/17809 | 3/2002 |
| WO | WO 02/24106 | 3/2002 |
| WO | WO 03/022159 | 3/2003 |
| WO | WO 03/026525 | 4/2003 |
| WO | WO 03/059152 | 7/2003 |
| WO | WO 03/061481 | 7/2003 |
| WO | WO 03/073944 | 9/2003 |
| WO | WO 03/077733 | 9/2003 |
| WO | WO 2004/086944 | 10/2004 |
| WO | WO 2004/086951 | 10/2004 |

(56) References Cited

FOREIGN PATENT DOCUMENTS

| WO | WO 2005/070316 | 8/2005 |
|----|----------------|--------|
| WO | WO 2005/070491 | 8/2005 |
| WO | WO 2005/0115231 | 12/2005 |

OTHER PUBLICATIONS

De Ponti, R., et al., "Trans-septal Catheterization for Radiofrequency Catheter Ablation of Cardiac Arrhythmias", The European Society of Cardiology, 19:943-950 (1998).

"Elastic Deployment", SMST-2000 Proceedings of the International Conference on Shape Memory and Superelastic Technologies, 3 pages (2000).

Hanson, James, et al., "Metals That Remember", Science 81, 44-47 Jun. 2005.

Kramer, Paul, M.D., "PFO and Stroke: The Hidden Connection", Endovascular Today, ((Apr. 2004).

Lavergne et al., "Transcatheter Radiofrequency Ablation of Atrial Tissue Using a Suction Catheter", Pace, vol. 12:177-186, Part II (1989).

Protsenko et al., "Electrosurgical Tissue Resection: A Numerical and Experimental Study", Proceedings of SPIE, vol. 4954:64-70, (2003).

Ruiz et al., "The Puncture Technique: A New Method for Transcatheter Closure of Patent Foramen Ovale", Catheterization and Cardiovascular Interventions, 53:369-372 (2001).

Sommer, et al., "New Transseptal Puncture Technique for Transcatheter Closure of Ovale", Mount Sinai Medical Center, (2002).

Stockel, "Nitinol Medical Devices and Implants", SMST-2000 Conference Proceedings, 531-541(2001).

Szili-Torok, "Transseptal Left Heart Catheterisation guided by Intracardiac Echocardiography", Heart 86:ell (2001).

* cited by examiner

REMOVABLE INTRACARDIAC RF DEVICE

CROSS-REFERENCE TO RELATED APPLICATION

This application is a divisional application of U.S. patent application Ser. No. 11/516,145, filed on Sep. 6, 2006, which claims priority to and the benefit of U.S. Provisional Patent Application Ser. No. 60/714,332, filed on Sep. 6, 2005. The entire contents of each of the above applications are incorporated by reference herein.

FIELD OF THE INVENTION

The invention generally relates to devices and related methods for treating intracardiac defects. More particularly the invention relates to devices for treating intracardiac defects with an energy source.

BACKGROUND OF THE INVENTION

The human heart is divided into four compartments or chambers. The left and right atria are located in the upper portion of the heart and the left and right ventricles are located in the lower portion of the heart. The left and right atria are separated from each other by a muscular wall, the intra-atrial septum, while the ventricles are separated by the intraventricular septum.

Either congenitally or by acquisition, abnormal openings, holes, or shunts can occur between the chambers of the heart or the great vessels, causing blood to flow therethrough. Such deformities are usually congenital and originate during fetal life when the heart forms from a folded tube into a four chambered, two unit system. The deformities result from the incomplete formation of the septum, or muscular wall, between the chambers of the heart and can cause significant problems. Ultimately, the deformities add strain on the heart, which may result in heart failure if they are not corrected.

One such deformity or defect, a patent foramen ovale, is a persistent, one-way, usually flap-like opening in the wall between the right atrium and left atrium of the heart. Since left atrial pressure is normally higher than right atrial pressure, the flap typically stays closed. Under certain conditions, however, right atrial pressure exceeds left atrial pressure, creating the possibility for right to left shunting that can allow blood clots to enter the systemic circulation. This is particularly worrisome to patients who are prone to forming venous thrombus, such as those with deep vein thrombosis or clotting abnormalities.

Nonsurgical (i.e., percutaneous) closure of a patent foramen ovale, as well as similar intracardiac defects such as an atrial septal defect, a ventricular septal defect, and ablation of the left atrial appendage, is possible using a variety of mechanical closure devices that are implanted into the anatomical site requiring treatment.

However, there are potential drawbacks to using a mechanical closure alone for the treatment of intracardiac defect. For example, some mechanical closures are prone to weakening and breakage. In addition, poor tissue ingrowth or improper positioning of the mechanical closure may lead to continued shunting of blood across the defect. Therefore, given the potential disadvantages of mechanical closures, there is a need in the art for correcting intracardiac defects by utilizing alternate methods. For example, tissue welding may be useful in correcting such defects. Tissue welding, a procedure wherein energy is applied to tissues to join them has been used to correct defects in the arteries, veins, bowel and nerves. Therefore, there is a need in the art for devices applying this technology to correct intracardiac defects.

SUMMARY OF THE INVENTION

The present invention provides systems and methods for treating an intracardiac defect through the delivery of energy. In one aspect, the system includes a device for delivering an energy delivery element to the site of the intracardiac defect. The energy delivery element delivers energy to the intracardiac defect. After delivery of energy, the energy delivery element is either left in place or removed from the site and the intracardiac defect is allowed to heal.

In one embodiment, the invention includes a removable device for occluding a patent foramen ovale (PFO). The removable device includes a sheath having a lumen, a proximal end and a distal end; an elongated member; and an energy delivery element. One of the sheath and the elongated member is axially movable relative to the other. The energy delivery element includes at least one coil having an electrode for delivering RF energy. The at least one coil includes at least a first loop and a second loop wherein the first loop has a diameter differing from the second loop. The energy delivery element is coupled to the elongated member to facilitate deployment and removal of said energy delivery element at the PFO. The energy delivery element is also operatively joined to an energy source.

In another embodiment, the invention includes a device for occluding a patent foramen ovale in patient including a sheath, an elongated member and an energy delivery element. The sheath includes a lumen, and at least one of the sheath and the elongated member is axially moveable relative to the other. The energy delivery element includes a first braided portion and a second braided portion separated by a non-braided portion. The energy delivery element is coupled to the elongated member to facilitate deployment and removal of the energy delivery element at the PFO.

In a further embodiment, the invention includes a medical device for occluding the tunnel of a patent foramen ovale in a patient including a sheath, an elongated member, and an energy delivery element including a plug. The sheath includes a lumen and one of the sheath and the elongated member is axially moveable relative to the other. The plug includes animal tissue and is joined to the elongated member. The plug also includes a core member sized and shaped to substantially fill the tunnel of the PFO.

In yet another embodiment, the invention includes a removable device for occluding a patent foramen ovale including a sheath, an elongated member and an energy delivery element. The sheath includes a lumen and one of the sheath and the elongated member is axially moveable relative to the other. The energy delivery element is coupled to the elongate member to facilitate deployment and removal of the energy delivery element at the PFO. The energy delivery element includes at least one curvilinear member with a releasable coating for bonding to the tissues of the PFO.

In another aspect, the invention provides a method for occluding a PFO using energy. For example, in one embodiment, a method for occluding a PFO includes passing a device through a PFO tunnel into a left atrium of a patient's heart. The device includes a sheath having a proximal end, a distal end, and a lumen; an elongated member; an energy delivering element including an occlusion shell; and an attachment device for attaching the elongated member to the energy delivery element. The elongated member and the sheath are axially moveable relative to the other. The energy delivery element includes an occluding member having at least one occlusion shell. The occluding member is deployed on the left atrial side of the PFO by retracting the sheath. Energy is applied to the PFO via the energy delivery element. The occluder is detached from the elongated member and the elongated member is then removed from the PFO.

BRIEF DESCRIPTION OF THE DRAWINGS

In the drawings, like reference characters generally refer to the same part throughout the different views. Also, the drawings are not necessarily to scale, emphasis instead generally being placed upon illustrating the principles of the invention.

FIG. 4A depicts a perspective view of the heart with the energy delivery element of FIG. 3 deployed in an intracardiac defect, while

DETAILED DESCRIPTION OF THE INVENTION

The present invention relates to a system for the repair of intracardiac defects, such as, for example, a patent foramen ovale, an atrial septal defect, a ventricular septal defect, and for obliteration of a left atrial appendage. The invention includes a system capable of delivering energy to an intracardiac defect, such as a patent foramen ovale. An energy delivery element is placed at the location of the intracardiac defect by a delivery catheter, and once appropriately positioned, the energy delivery element delivers energy from an energy source that welds tissues of the defect together, occluding any openings. The term "weld" as it is used throughout this application means sealing together either completely or substantially. The energy delivery element can be removed in its entirety after delivery of energy or alternatively, a portion or portions of the energy delivery element can be permanently implanted in the area of the defect after delivery of energy. Welding of the tissues can occur after the energy delivery element is removed, or while the energy delivery element is positioned in the intracardiac defect.

Figure 1:
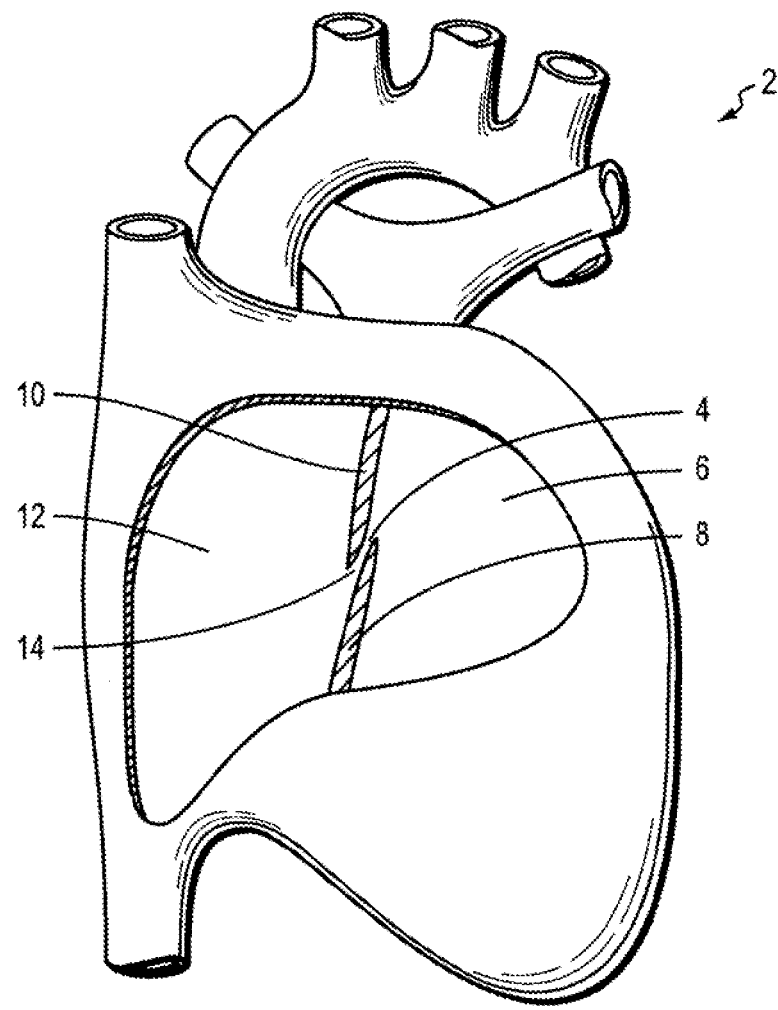
FIG. 1 depicts a cutaway view of the heart illustrating an intracardiac defect.

FIG. 1 depicts a cutaway view of a heart 2. The heart 2 includes a septum 4 that divides the right atrium 12 from the left atrium 6. The septum 4 includes a septum primum 8, a septum secundum 10, and an exemplary intracardiac defect 14, which is corrected by the delivery of energy to the area by the system according to the invention. Specifically, a patent foramen ovale 14 is shown as an opening through the septum 4. The patent foramen ovale 14 provides an undesirable communication between the right atrium 12 and the left atrium 6. Under certain conditions, a patent foramen ovale 14 in the septum 4 permits shunting of blood from the right atrium 12 to the left atrium 6. If the patent foramen ovale 14 is not closed or obstructed in some manner, a patient is placed at high risk for an embolic stroke, migraine, or other pathological condition.

Delivery System

Figure 2:
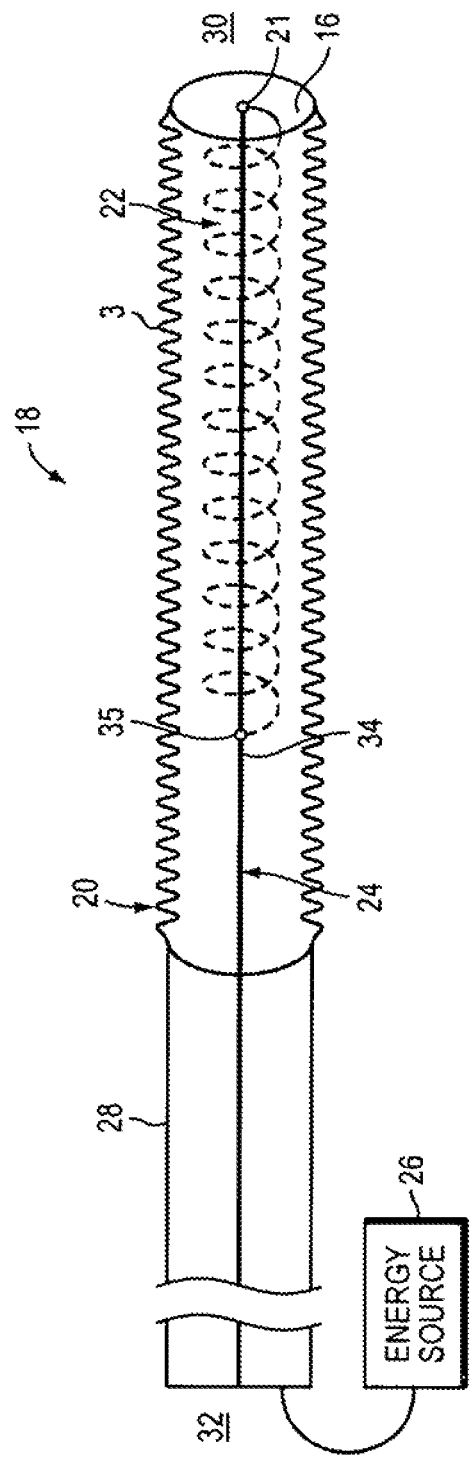
FIG. 2 shows a perspective view of a system for delivering energy to an intracardiac defect, according to an illustrative embodiment of the invention.

FIG. 2 shows a perspective view of a system for delivering energy to an intracardiac defect according to an illustrative embodiment of the invention. The system 18 includes a delivery catheter 28 including a lumen 16 and an energy delivery element 22. The energy delivery element 22 comprises at least one electrode (not shown). In another embodiment the system 18 includes an introducer sheath (not shown) and a guidewire (not shown). In one embodiment, the energy delivery element 22 is maintained within the delivery catheter 28 until the energy delivery element 22 is deployed at the site of the intracardiac defect 14, for example, a patent foramen ovale.

In another embodiment, the system 18 further includes an energy source 26. The energy source 26 can provide one or more of any number of energy types including, but not limited to microwave energy, infrared energy, visible light waves, ultraviolet rays, x-rays, gamma rays, cosmic rays, acoustic energy, thermal energy, or radio frequency energy. In a preferred embodiment, the energy source 26 provides radio frequency energy (RF) for the system 18. For example, the energy source 26 is connected directly to the energy delivery element 22, in one embodiment, while in another embodiment, it is connected to the delivery catheter 28 or a component of the delivery catheter 28 to which the energy delivery element 22 is connected. Alternate modes of coupling the energy source 26 to the energy delivery element 22 will be obvious to one of skill in the art and are within the scope of the invention.

Referring again to FIG. 2, the delivery catheter 28 has a proximal end 32 and a distal end 30. In one embodiment, the delivery catheter 28 is housed within a catheter (not shown) having an actuating member (not shown) for effecting movement of the delivery catheter 28. In another embodiment, the delivery catheter 28 is coaxially associated with a catheter (not shown) having an actuating member (not shown) for effecting movement of the delivery catheter 28. In one embodiment, an actuating member is operatively connected to the proximal end 32 of the delivery catheter. In another embodiment, the actuating member is connected to a wire or rod or cable (not shown) that is connected to the proximal end 32 of the delivery catheter. An operator moves the actuating member proximally 32 to move the delivery catheter in a proximal direction, for example, or moves the actuating member distally 30 to move the delivery catheter distally 30, according to one embodiment of the invention.

With continued reference to FIG. 2, in one embodiment, the delivery catheter 28 further includes a cable 24 which attaches, engages or connects to the energy delivery element 22. The cable 24 is in one embodiment, for example, a wire while in another embodiment, it is a rod. The cable 24 is capable of movement in one or more of the proximal (towards the operator) and distal (away from the operator) directions. For example, in one embodiment, movement of the cable 24 is facilitated by an actuating member (not shown) operatively connected to the cable 24. For example, in one embodiment, the operator moves the actuating member proximally to move the cable 24 proximally, while in another embodiment, the operator moves the actuating member distally to move the cable 24 distally.

In one embodiment, the energy delivery element 22 is permanently connected to the cable 24 at the distal end 21 of the energy delivery element 22. For example, the distal end of the cable 24 is connected to the distal end 21 of the energy delivery element 22. In another embodiment, the energy delivery element 22 is permanently connected to the cable 24 at the proximal end 34 of the energy delivery element 22. For example, the distal end of the cable 24 is connected to the proximal end 34 of the energy delivery element 22.

In another embodiment, the energy delivery element 22 is releasably connected to the cable 24 at the proximal end 34 of the energy delivery element 22 by a releasable attachment (not shown), while in another embodiment, the energy delivery element 22 is releasably connected to the cable 24 at the distal end 21 of the energy delivery element 22 by a releasable attachment (not shown). Examples of releasable attachments suitable for connecting the energy delivery element 22 to the cable 24 include, but are not limited to, for example, ball-rod connections, ball-claw connections, threaded connections, looped connections, magnetic connections, male-female connections, adhesive connections, clamped connections, and hook-eye connections.

Referring still to FIG. 2, in order to prevent the system 18 from contacting and energizing blood within the chambers of the heart resulting in blood clotting or other negative side effects, at least a portion of the system 18 is insulated. For example, in one embodiment the delivery catheter 28 is insulated. In a further embodiment, the insulated delivery catheter 28 is manufactured from a non-conductive material. In another embodiment, the cable 24 is insulated. In a further embodiment, the insulated cable 24 is manufactured from a non-conductive material.

In a further embodiment, the energy delivery element 22 is releasably connected to the cable 24 and the releasable attachment point 36 is insulated. For example, in one embodiment a non-conductive insulating material is provided in the form of a coating, a temporary sleeve, a permanent sleeve, or an extrusion on or surrounding the releasable attachment 36 at and/or around the connection point 36. Likewise, other portions of the system 18 that contact the blood should be appropriately insulated with a non-conductive material. Those portions of the system 18 that are insulated can be insulated by a temporary or permanent non-conductive coating or sleeve. Examples of non-conductive materials that may be used for these purposes include one or more polymers.

With continued reference to FIG. 2, in a further embodiment, the delivery catheter 28 has a delivery sheath 20. The delivery sheath 20 includes a lumen 16. The delivery sheath 20 houses the energy delivery element 22 in the lumen 16 until it is deployed at the site of an intracardiac defect 14. In one embodiment, the proximal end of the delivery sheath 20 is fixed to the distal end of the delivery catheter 28, while in another embodiment, the proximal end of the delivery sheath 20 is movable relative to the distal end of the delivery catheter 28. For example, in one embodiment, at least a portion of the sheath 20 can be retracted into the lumen 16 of the delivery catheter 28, while in another embodiment, the entire sheath 20 can be retracted into the lumen 16 of the delivery catheter 28.

The delivery sheath 20 is attached to a wire or cable or rod (not shown) to permit movement of the delivery sheath in the proximal 30 and distal 32 directions. For example, in one embodiment the proximal end of the delivery sheath 20 is attached to a wire or cable or rod (not shown) that is coaxial with or parallel to cable 24. In another embodiment, the distal end 30 of the delivery sheath 20 is attached to a wire or cable or rod coaxial with or parallel to cable 24. In one embodiment, the wire, cable or rod attached to the delivery sheath 20 is operatively connected to an actuating member (not shown). An operator moves the sheath 20 proximally or distally by moving the actuating member proximally or distally, respectively, according to one embodiment of the invention.

In order to deploy the energy delivery element 22 positioned inside the lumen 16 of catheter 28, in one embodiment, an operator positions the distal end 30 of the delivery catheter 28 appropriately in the intracardiac defect 14, and then retracts the delivery catheter 28 proximally, deploying the energy delivery element 22 at the site of an intracardiac defect 14. In an alternate embodiment, the operator advances the cable 24 beyond the distal end 30 of the delivery sheath 20, and deploys the energy delivery element 22. Optionally, the energy delivery element 22 may be recaptured by the sheath 20 and removed after delivery of energy to the intracardiac defect 14. In another embodiment, the energy delivery element 22 may be recaptured by the delivery catheter 28.

Optionally, if the energy delivery element 22 is permanently placed in the intracardiac defect 14, the energy delivery element 22 is released from the cable 24 by releasing the releasable attachment 36 at the attachment point after delivery of energy to the intracardiac defect 14. While the aforementioned embodiments of the delivery system 18 are useful for delivering the energy delivery element 22 to an intracardiac defect, any suitable delivery system known to one of skill in the art may be utilized.

Energy Delivery Element

Figure 3:
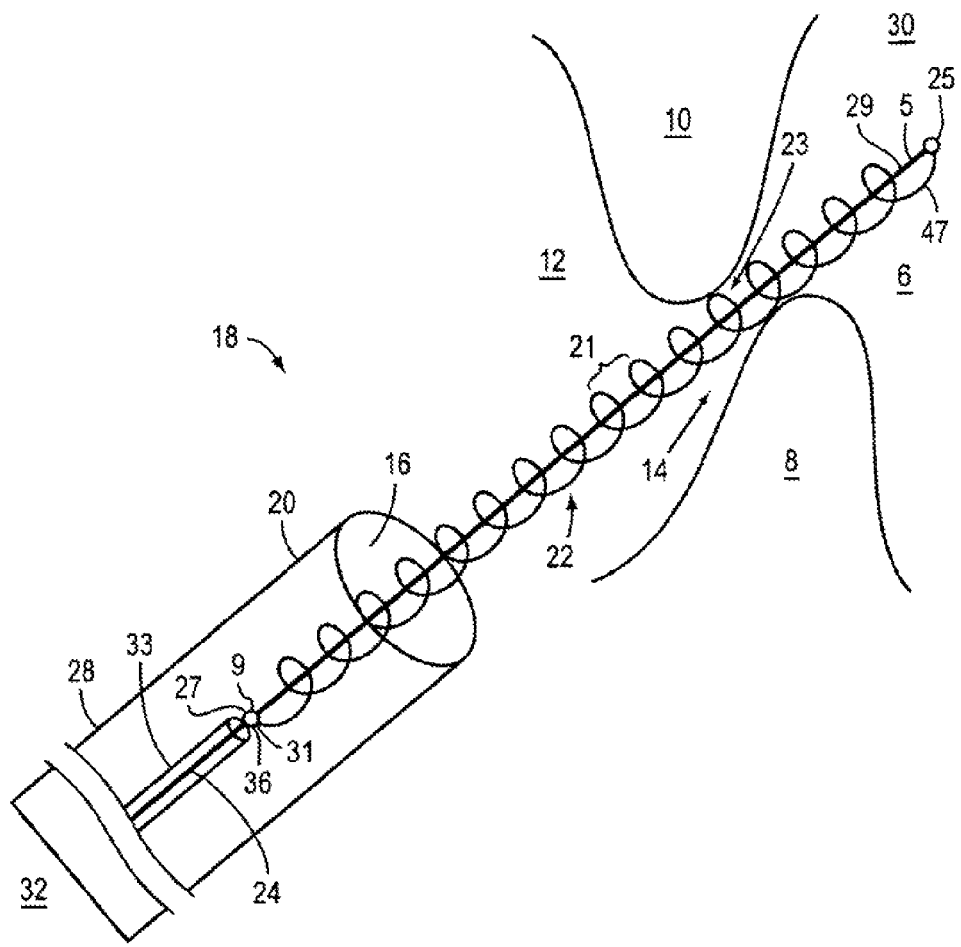
FIG. 3 depicts an energy delivery element including a coil having a plurality of loops coiled or wrapped around a central post, according to an illustrative embodiment of the invention.

FIG. 3 depicts an energy delivery element including a coil having a plurality of loops coiled or wrapped around a central post, according to another illustrative embodiment of the invention. As shown in FIG. 3, the energy delivery element 22 is positioned in the tunnel 23 of a patent foramen ovale 14. The energy delivery element 22 includes at least one coil 47 and a central post 29 that is axially disposed in the lumen of the loops 21 of the coil 47. The central post 29 is a continuation of the cable 24 in one embodiment, while in another embodiment, the central post 29 is a separate member that is joined to the cable 24. For example, in one embodiment, the distal end of the cable 24 is connected to the proximal end of the central post 29.

A coil 47, according to the invention, comprises at least one loop 21, but may comprise a plurality of loops. A loop 21 is a full turn of the coil 47. For example, in one embodiment, the coil 47 of the energy delivery element 22 comprises at least one spiral loop 21, i.e., a full turn of a continuous curve traced by a point moving around a fixed point in the same plane while steadily increasing or diminishing its distance from the fixed point (like a watch spring). In another embodiment, the coil 47 of the energy delivery element 22 comprises at least one helical loop 21, i.e., a full turn of a continuous curve traced by a point moving around a fixed point along an axis (like a cork screw). The diameter of the helical loops 21 of the coil 47, may increase, decrease or stay the same along the axis of the coil 47. In another embodiment, the energy delivery element 22 has two loops, while in a further embodiment, the energy delivery element 22 has 3, 4, 5, 6, 7, 8, 9, 10 or more loops. In addition, the coil 47 is a right hand coil in one embodiment, while it is a left hand coil in a second embodiment. In a further embodiment, the coil 47 contains at least one right-handed loop 21 and at least one left-handed loop 21.

With continued reference to FIG. 3, in one embodiment, the distal end 5 of the central post 29 is connected to the distal end 25 of the coil 47, and the proximal end 9 of the central post 29 is attached to proximal end 27 of the coil 47. In an alternate embodiment, the distal end 5 of the central post 29 is attached to the distal end 25 of the coil 47, while the proximal end 27 of the coil 47 is slideably moveable along the central post 29 from the proximal end 9 of the central post towards the distal end 25 of the central post. In yet another embodiment, the proximal end 7 of the central post 29 is attached the proximal end 27 of the coil 47, while the distal end 25 of the coil 47 is slideably moveable along the central post 29 from the distal end 25 of the central post 29 towards the proximal end 9 of the central post 29.

In one embodiment, the central post 29 is releasably joined to the coil 47 at either one or both of the proximal end 9 and distal end 5 of the central post 29 by a releasable attachment (not shown).

With continued reference to FIG. 3, in a particular embodiment, the system 18 includes a push rod 33 coaxial with the central post 29 or, in an alternative embodiment, parallel thereto (not shown). The push rod 33 is slidably moveable in the lumen 16 of the delivery catheter 28. The push rod 33 can be a hollow or solid rod or wire. In one embodiment, the push rod 33 is coaxial with the cable 24. In a further embodiment, the push rod 33 is directly connected to the proximal end 27 of the coil 47, while in yet a further embodiment, the push rod 33 engages the proximal end 27 of the coil 47 when moved distally along the central post 29. For example, in one embodiment, a hollow push rod 33 coaxial with the cable 24 is moved distally to engage a ball 31 at the proximal end 27 of the coil 47.

Figure 4A:
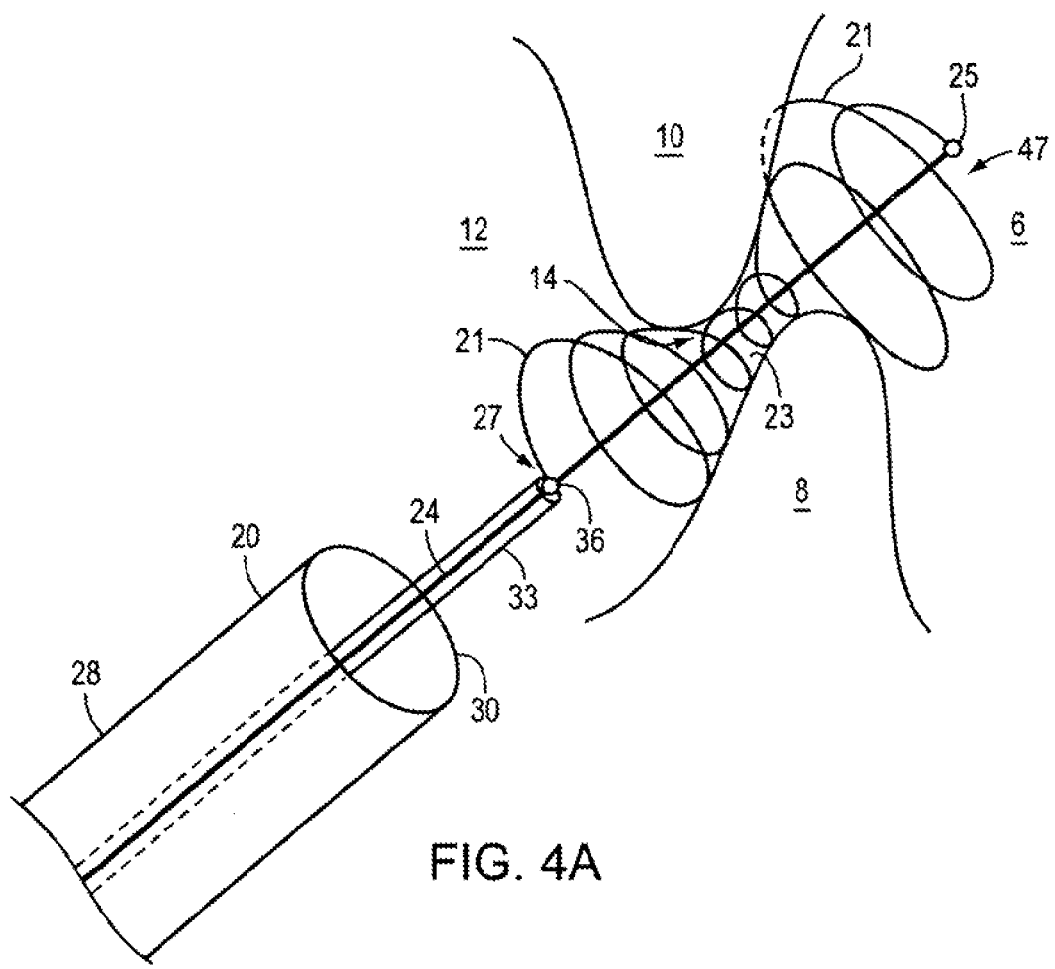
Figure 4B:
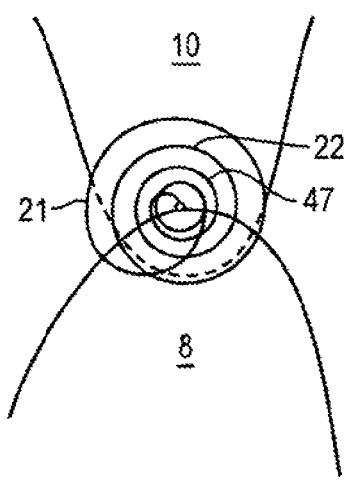
FIG. 4B shows a left atrial view of the deployed energy delivery element as shown in FIG. 4A, according to an illustrative embodiment of the invention.

FIG. 4A depicts a perspective view of the heart with energy delivery element of FIG. 3 deployed in an intracardiac defect while FIG. 4B shows a left atrial view of the deployed energy delivery element as shown in FIG. 4A, according to an illustrative embodiment of the invention. An operator introduces the delivery catheter 28 via a transluminal percutaneous approach through, for example, the femoral vein. Next, the operator moves the delivery catheter 28 to the right atrium 12 and positions the catheter 28 in the tunnel 23 of the patent foramen ovale 14. In a further embodiment, the distal end 30 of the delivery catheter 28 is positioned in the left atrium 6, while the proximal end is positioned in the right atrium 12.

In order to deploy the energy delivery element 22, the energy delivery element 22 must be released from the confines of the delivery catheter 28. In one embodiment, for example, the delivery catheter 28 is retracted proximally to expose the energy delivery element 22. In another embodiment, the energy delivery element 22 is advanced beyond the distal end 30 of the catheter 28 to deploy the energy delivery element 22. In another embodiment, the operator retracts the catheter 28 and any delivery sheath (not shown) to reveal the central post 29 and coil 47 of the energy delivery element 22.

To deploy the energy delivery element 22, in one embodiment the operator moves the push rod 33 distally causing the loops 21 of the energy delivery element 22 expand at the intracardiac defect 14. In an alternative embodiment, the push rod 33 remains stationary while the operator retracts the central post 29 proximally, also causing the loops 21 of the energy delivery element 22 to expand. For example, in one embodiment, in a deployed state, at least one loop 21 of the coil 47 of the energy delivery element 22 has a diameter that is larger than the diameter of the at least one loop 21 in an undeployed state. In yet another embodiment, in a deployed state the length of the axis of coil 47 from the proximal end 27 to the distal end 25 is decreased as compared to the length of the axis of the coil 47 in an undeployed state.

In one embodiment, the loops 21 of the energy delivery element 22 are deployed in the left atrium 6 and right atrium 12. In another embodiment, the loops 21 of the energy delivery element 22 are deployed only in the left atrium 6.

After energy is delivered to the patent foramen ovale 14, including the septum primum 8, the septum secundum 10, or both, in one embodiment, the operator moves the push rod 33 proximally to collapse the loops 21 of the of the energy delivery element 22 to their original size, for removal from the intracardiac defect 23. In an alternate embodiment, the operator moves the central post 29 distally while keeping the push rod 33 stationary to collapse the loops 21 of the energy delivery element 22.

With continued reference to FIG. 3, in yet another embodiment, the system 18 includes a pull wire (not shown). The pull wire can be a hollow or solid rod or wire. In one embodiment, the pull wire is coaxial with the central post 29, while in another embodiment, the pull wire is parallel to the central post 29. In another embodiment, the pull wire is connected to the distal end 25 of the energy delivery element 22. The connection between the energy delivery element 22 and the pull wire is fixed in one embodiment, while in another embodiment, the pull wire engages the distal end 25 of the energy delivery element 22 when moved proximally along the central post 29.

In a further embodiment, the system 18 includes a pull wire (not shown) and a push rod 33. The push rod 33, in one embodiment, is coaxial with the pull wire, while in another embodiment, the push rod 33 is parallel with the pull wire. In a further embodiment, the push rod 33 is attached to the proximal end of the energy delivery element 22 while the pull wire is attached to the distal end of the energy delivery element.

To deploy the energy delivery element 22, in one embodiment the operator retracts the pull wire proximally causing the loops 21 of the energy delivery element 22 to expand at the intracardiac defect 14. In another embodiment, the operator moves the push rod 33 distally and the pull wire proximally causing the loops 21 of the energy delivery element 22 to expand at the intracardiac defect 14. In a further embodiment, the operator twists the push rod 33 to the right or to the left (depending on whether the coil 47 has right hand or left hand loops, respectively) while moving the push rod 33 distally along the cable 24, to improve the extension of the loops 21 of the energy delivery element 22, i.e., to increase the diameter of the loops 21 of the coil 47. In yet another embodiment, the operator twists the push rod 33 while moving the push rod 33 distally and twists the pull wire as it moves proximally along the cable 24 to improve the extension of the loops 21.

After energy is delivered to the patent foramen ovale 14, including the septum primum 8, the septum secundum 10, or both, in one embodiment, the operator moves the push rod 33 proximally, and if necessary, moves the central post 29 distally to collapse the loops 21 of the energy delivering elements 22 to their original size, for removal from the intracardiac defect 23.

After energy is delivered to the patent foramen ovale 14, including the septum primum 8, the septum secundum 10, or both, according to one embodiment, the operator moves the pull wire distally to elongate the loops 21 to their original size prior to deployment. In another embodiment, the operator moves the push rod 33 proximally and the pull wire distally to elongate the loops 21 of the of the energy delivering element 22 to their original size, for removal from the intracardiac defect 23.

According to an illustrative embodiment of the invention, FIG. 4A depicts a perspective view of the heart with the energy delivery element of FIG. 3 deployed in an intracardiac defect, while FIG. 4B shows a left atrial perspective view of the deployed energy delivery element as shown in FIG. 4A. After an operator introduces the delivery catheter 28 via a transluminal percutaneous approach through, for example, the femoral vein to the right atrium 12, the operator positions the delivery catheter 28 at the site of the intracardiac defect 14 and deploys the energy delivery element 22 in the tunnel 23 of the patent foramen ovale.

For example, in on embodiment, deploying the energy delivery element 22 includes the step of removing the energy delivery element 22 from the confines of the delivery sheath 20. In one embodiment, for example, the sheath 20 is retracted proximally to expose the energy delivery element 22, while in another embodiment, the energy delivery element 22 is advanced distally beyond the distal end 30 of the sheath 20.

In another embodiment, deployment of the energy delivery element 22 includes the step of disconnecting the proximal end of coil 47 of the energy delivery element 22 from the attachment point 36, causing the loop or loops 21 to unfurl and expand on both the left atrial 6 and right atrial 12 sides of the patent foramen ovale 14. Once deployed, the loops 21 on both the left atrial 6 and right atrial 12 sides of the tunnel 23 of the patent foramen ovale 14 appose the septum secundum 10 and the septum primum 8 allowing them to weld to one another upon application of energy to this anatomical site through the energy delivery element 22 as shown in FIG. 4B.

Alternately, in another embodiment, the loops 21 of the energy delivery element 22 are deployed only on the left atrial side 6 of the patent foramen ovale 14. With the energy delivery element 22 deployed at the patent foramen ovale 14, energy is applied through the energy delivery element 22 to the septum primum 8 and septum secundum 10. The energy delivery element 22 is optionally removed by retracting the cable 24. The cable 24 is attached to the distal end of the central post 29. The central post 29 remains attached to energy delivery element 22 at least the distal end point 25.

As shown in FIG. 4A and FIG. 4B, once deployed, the loops 21 of the energy delivery element 22 can have varying diameters. This allows the energy delivery element 22 to contact a larger surface area of the intracardiac defect 14. Preferably the loops 21 are made of a shape memory alloy, such as nitinol, which allows them to be retained in a catheter 28 at one size prior to deployment and upon release, allows them to expand to a predetermined larger size. For example, in one embodiment, at least one loop 21 of the coil 47 has a first smaller diameter in an undeployed state and has a second larger diameter in a deployed state. In another embodiment, each loop 21 of coil 47 has the same first diameter in the undeployed state and the same second diameter in the deployed state. In another embodiment, at least two loops 21 of coil 47 differ in their diameter in the deployed state.

Referring now to FIG. 3, and with continued reference to FIG. 4A, the length of coil 47 varies from the undeployed state to the deployed state. For example, as shown in FIG. 3, the length of coil 47, shown in an undeployed state, is longer than the length of coil 47, shown in FIG. 4A in a deployed state, wherein the length is the measurement of the axis of the coil 47 from the proximal end to the distal end of the coil 47. According to the invention, in one embodiment, a coil 47 has a first shorter length in an undeployed state and moves to a second longer length in the deployed state.

Referring to FIG. 4A, in order to avoid coagulation of the blood and other complications, according to one embodiment, the deployed energy delivery element 22 is insulated. For example, at least a portion of a loop or loops 21 is coated with a non-conductive insulating material. In another embodiment, at least a portion of a loop 21 that touches the septum primum 8 and/or septum secundum 10 or that is configured to deliver energy to the septum primum 8 and/or septum secundum 10 is not coated, while the portion of the loop 21 that does not directly contact the septum primum 8 and/or septum secundum 10, but rather would be in contact with atrial blood is coated with a non-conductive coating. In another embodiment, some loops 21 are insulated while other loops 21 are uninsulated. In one embodiment, the insulation is provided by a non-conductive coating in the form of a sleeve. In another embodiment, the non-conductive coating is made of a polymer.

Figure 5:
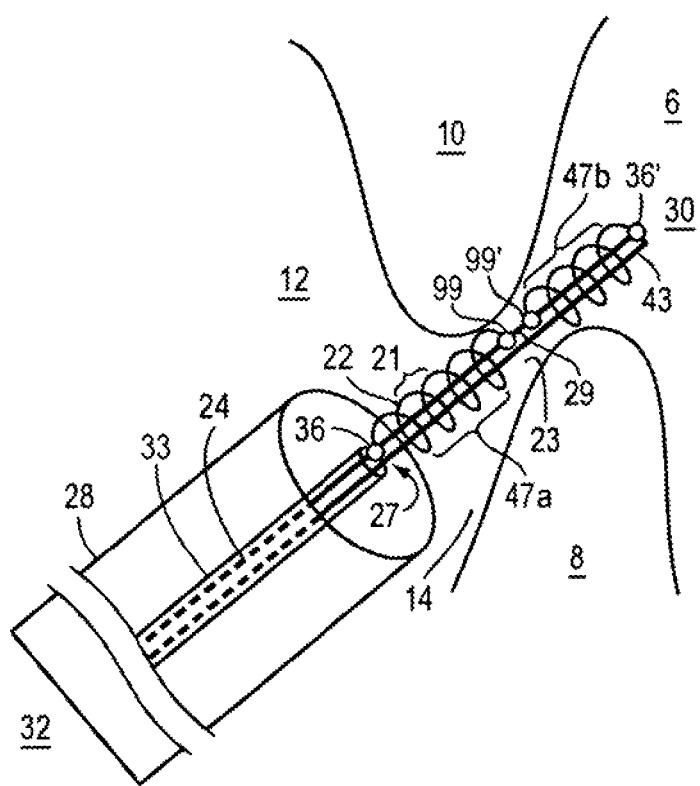
FIG. 5 depicts another system for delivering energy to an intracardiac defect including an energy delivery element with a plurality of coils according to an illustrative embodiment of the invention.

FIG. 5 depicts another system for delivering energy to an intracardiac defect including an energy delivery element with a plurality of coils according to an illustrative embodiment of the invention. The exemplary energy delivery element 22 includes two coils 47a, 47b (collectively 47). According to one embodiment, each coil 47 includes at least one loop 21; however, the coils 47 may include two, three, four, five, six, or more loops 21. According to one embodiment, each coil 47 has the same number of loops 21, while in another embodiment one coil 47a has a different number of loops 21 from the other coil 47b. Each coil 47 of the energy delivery element 22 has an electrode (not shown), according to one embodiment of the invention, while in another embodiment of the invention, a coil 47a, 47b, may have one or more electrodes, for example, 2, 3, 4, 5, 6 or more electrodes.

With continued reference to FIG. 5, in one embodiment, a proximal coil 47a deploys on the right atrial side 12 of the defect 14 while the distal coil 47b deploys on the left atrial side 6 of the defect 14. In one embodiment, the proximal coil 47a and the distal coil 47b are two separate coils while in another embodiment. For example, proximal coil 47a is fixed at its distal end to central post 29 at connection point 99, while distal coil 47b is fixed at its proximal end to central post 29 at connection point 99'. In an alternate embodiment, the proximal coil 47a and the distal coil 47b are contiguous with or joined to one another.

In a further embodiment, the proximal end of the proximal coil 47a connects at connection point 36 to a push rod 33 which optionally twists axially, while the distal end of the distal coil 47b connects at connection point 36' to a pull back wire or rod 43 which also optionally twists axially. In one embodiment, the connection 36 between the push rod 33 and the proximal coil 47a is fixed, while in another embodiment the connection 36 is releasable. For example, in one embodiment, the push rod 33 engages a ball on the proximal end 27 of coil 47a to allow the push rod 33 to actuate movement of the coil 47a. In another embodiment, the connection 36' between the distal coil 47b and the pull back rod or wire 43 is fixed, while in another embodiment, the connection 36' is releasable. For example, in one embodiment, the pull back rod or wire 43 engages a ball on the distal end of coil 47b to actuate movement of the coil 47b.

In one embodiment, the push rod 33 and pull back rod 43 are parallel to one another. In another embodiment, the push rod 33 and pull rod 43 are coaxial with one another. In a further embodiment, the push rod 33 and pull back rod 43 are parallel to the cable 24, and may alternatively be coaxial with the cable 24. According to one embodiment of the invention, movement of the push rod 33 distally elongates and deploys the loops 21 of the proximal coil 47a, while movement of the pull wire proximally 27 elongates and deploys the loops 21 of the distal coil 47b. For example, in one embodiment, at least one loop 21 of each of coil 47a and 47b has a first smaller diameter prior to deployment and a second larger diameter after deployment.

With continued reference to FIG. 5, after energy is delivered to the intracardiac defect 14, including the septum primum 8 and the septum secundum 10, the push rod 33 is moved proximally, and the pull back wire 43 is moved distally to collapse the loops 21 of coils 47a and 47b of the energy delivering element 22 for removal from the intracardiac defect 14.

With reference to FIGS. 3, 4A-B, and 5, a coil 47 in one embodiment is made of a shape memory alloy, for example, nitinol. In one embodiment, coil 47 of energy delivery element 22 is maintained in an uncoiled state within delivery sheath 20. The energy delivery element 22 forms a coiled state upon deployment. For example, in one embodiment, the energy delivery element 22 forms a coiled state when released from the confines of the delivery sheath 20. In another embodiment, the energy delivery element 22 forms a coiled state from an uncoiled state when the energy delivery element is actuated by, for example, a push rod 33 or a pull rod 43. For example, in one embodiment, when the proximal end of the energy delivery element 22 is moved distally by push rod 33, the energy delivery element 22 moves from an uncoiled state to a coiled state.

Figure 6:
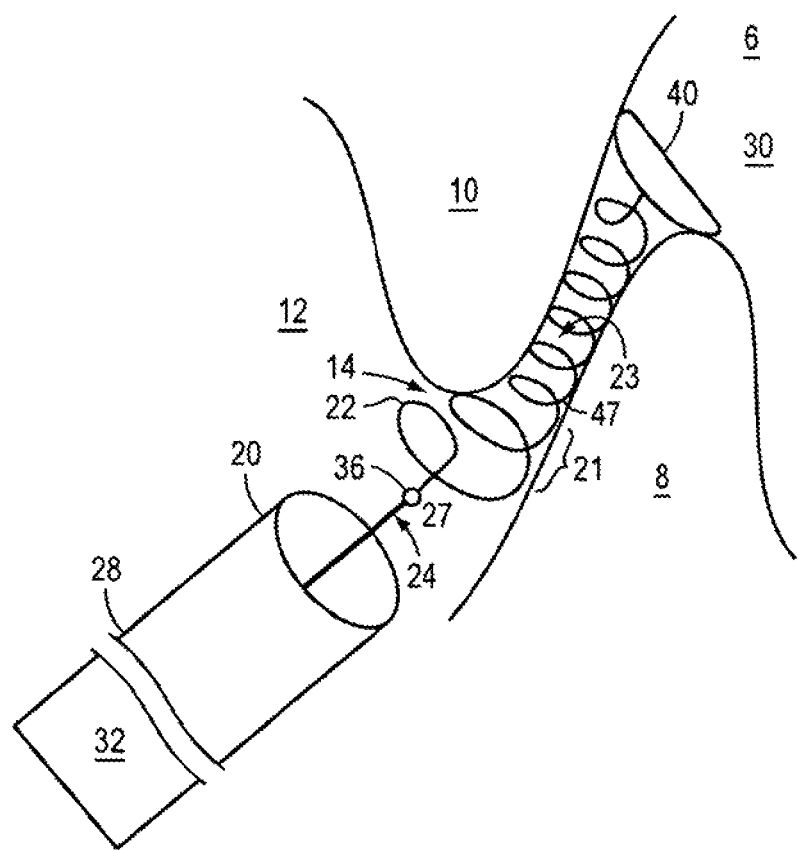
FIG. 6 depicts a perspective view of an energy delivery element including a locator according to an illustrative embodiment of the invention.

FIG. 6 depicts a perspective view of an energy delivery element including a locator, according to an illustrative embodiment of the invention. As shown in FIG. 6, the energy delivery element 22 includes a series of loops 21 forming a coil 47. In one embodiment, the energy delivering element 22 includes a locator 40 for locating the intracardiac defect 14 and for apposing the septum primum 8 and septum secundum 10 on the left atrial side 6 of the defect 14. In one embodiment, the locator 40 is positioned at the distal end of the energy delivery element 22.

Prior to deployment, the loops 21 of the energy delivery element 22 are maintained in a collapsed state inside the delivery catheter 28. To deploy the energy delivery element 22, the operator introduces the delivery catheter 28 into the left atrium 6 through the tunnel 23 of the patent foramen ovale 14 and deploys the locator 40. In one embodiment, the operator deploys the locator on the left atrial side 6 by retracting the delivery catheter 28, and if necessary, any delivery sheath 20 enclosing the locator 40. In another embodiment, the operator deploys the locator 40 by pushing the locator 40 portion of the energy delivery element 22 distally beyond the distal end of the delivery catheter 28 and if necessary, any portion of a delivery sheath 20 housing the locator 40. The remaining loops 21 of the energy delivery element 22 not comprising the locator remain inside the delivery catheter 28 in a collapsed state until their subsequent deployment.

To deploy loops 21 not comprising the locator 40, the operator moves the delivery catheter proximally so that the locator 40 abuts the septal wall of the left atrium 12. Next, the operator then retracts the delivery catheter 28 and any delivery sheath 20 housing the loops 21 to expose the remaining loops 21 in the tunnel 23. In an alternate embodiment, the locator 40 and the loops 21 of the energy delivery element 22 are exposed in the left atrium 6 and then moved into the tunnel 23 after deployment.

The locator 40 of the energy delivery element 22 apposes the septum primum 8 and septum secundum 10 to improve closure of the defect 14 by abutting the left atrial septal wall. After the locator 40 and loops 21 of the energy delivery element 22 are appropriately positioned, energy is delivered to the defect. In one embodiment the locator 40 is insulated, while in another embodiment, the locator 40 transfers energy to the septum primum 8 and septum secundum 10. Once energy has been delivered, the energy delivery element 22 is recaptured by the delivery catheter 28 and removed from the patent foramen ovale 14. The septum primum 8 and septum secundum 10 then weld together.

While FIG. 6 depicts a disc-shaped locator 40 circular in shape, a locator may be of any useful geometrical shape such as, but not limited to, an oval, a sphere, an ellipse, a rectangle, a triangle, a square, or a star shape. For example, in one embodiment, the locator 40 is a wire or wires shaped into, for example, any of the aforementioned geometrical shapes, while in another embodiment, the locator 40 is a solid body such as a sphere or disc. In another embodiment, the locator is coil shaped. In yet another embodiment, the locator 40 is a wire sized and shaped to serve as a frame for a fabric or wire mesh. In a further embodiment, a locator 40 is attached to the distal end of any of the various embodiments of energy delivery elements 22 described in this application.

Figure 7:
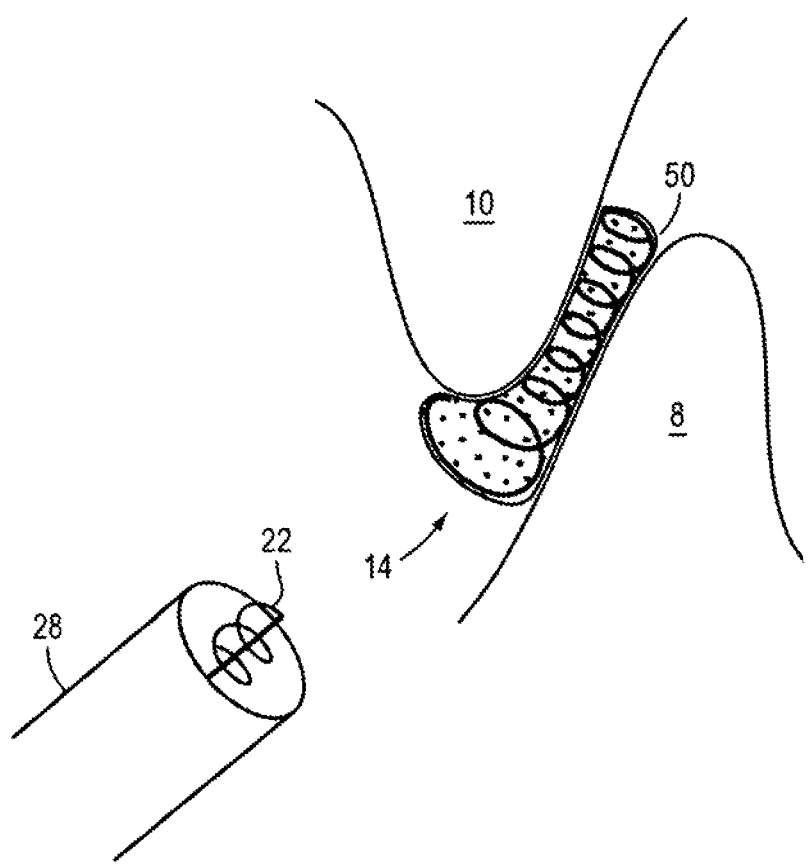
FIG. 7 depicts an implant deposited in an intracardiac defect by the energy delivery element of FIG. 6, according to an illustrative embodiment of the invention.

FIG. 7 depicts an implant positioned in an intracardiac defect by the energy delivery element of FIG. 6 according to an illustrative embodiment of the invention. As shown in FIG. 7, in one embodiment, an implant 50 remains in the tunnel 23 of the patent foramen ovale 14 after the energy delivery element 22 and catheter 28 have been removed. The implant 50 is a coating or sleeve placed on the surface of the energy delivery element 22, which is released from the energy delivery element and remains in the tunnel 23 upon removal of the energy delivery element 22, according to one embodiment of the invention.

In one embodiment, the implant 50 is an adhesive member, e.g., a plug of adhesive that adheres to septum primum 8 and septum secundum 10 to improve tissue apposition and closure of the patent foramen ovale 14. In another embodiment, the implant 50 includes one or more of a polymer, a bioabsorbable material, a growth stimulating material, or a metal with a low melting point. In a further embodiment, the implant 50 includes an animal tissue, for example, such as intestinal submucosa, urinary bladder basement membrane or collagen. According to the invention, an implant coating or sleeve 50 as described herein can be placed on any of the embodiments of energy delivery elements 22 described in this application.

The implant 50, according to one embodiment, adheres to the septum primum 8 and septum secundum 10 and is released from the energy delivery element 22 when the energy delivery element 22 is retracted after energy is applied to the intracardiac defect 14. In one embodiment, the plug is sized and shaped to substantially fill the patent foramen ovale 14. According to one embodiment, the implant 50 expands to fill the patent foramen ovale 14 upon application of energy.

Figure 8:
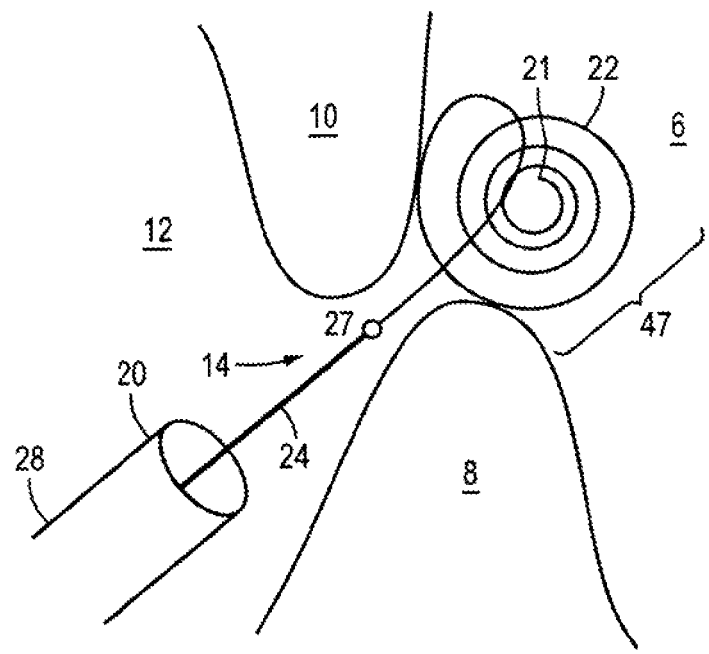
FIG. 8 depicts a perspective view of a coiled device for delivering energy to the left atrial side of an intracardiac defect according to an illustrative embodiment of the invention.

FIG. 8 depicts a perspective view of a coiled device for delivering energy to the left atrial side of an intracardiac defect according to an illustrative embodiment of the invention. As shown in FIG. 8, the coiled energy delivery device 22 of the invention is, for example, a wire. In one embodiment, the wire is an extension of cable 24, while in another embodiment, the wire is attached to the distal end 27 of the cable 24. For example, in one embodiment, the proximal end of the coiled energy delivery element 22 is connected with the cable 24 at the cable's distal end while the distal end of the coiled energy delivery element 22 is a free end.

With continued reference to FIG. 8, in one embodiment, the energy delivery element 22, is made of a metal with shape memory properties, such as nitinol. Shape memory properties allow the loops 21 of the energy delivery element 22 to enlarge from a collapsed state at body temperature upon removal of the catheter 28. For example, in one embodiment, when the energy delivery element 22 is maintained within catheter 28, it is in an uncoiled state, whereas when energy delivery element 22 is deployed beyond the distal end of the catheter 28, the energy delivery element 28 forms a coiled state, for example, as shown in FIG. 8.

In order to deploy the energy delivery element 22, for example, shown in FIG. 8, the delivery catheter 28 is appropriately positioned at the intracardiac defect and the energy delivery element 22 is deployed. In one embodiment, the energy delivery element 22 is deployed by relative movement between the energy delivery element 22 and the delivery catheter 28. For example, the delivery catheter 28 is retracted proximally to expose the energy delivery element 22, in one embodiment. In another embodiment, the energy delivery element 22 is deployed by advancing the energy delivery element 22 distally beyond the distal end of delivery catheter 28 and any sheath 20 that encloses the energy delivery element 22.

As shown in FIG. 8, the loops 21 of the energy delivery element 22 are deployed in the left atrium 6. The loops 21 appose the septum primum 8 and septum secundum 10. After deployment, energy is delivered to the septum primum 8 and septum secundum 10 by the loops 21 and to the tunnel 23 by the non-coiled portion 37 of the energy delivery element 22. Subsequently, the energy delivery element is 22 is removed.

Figure 9:
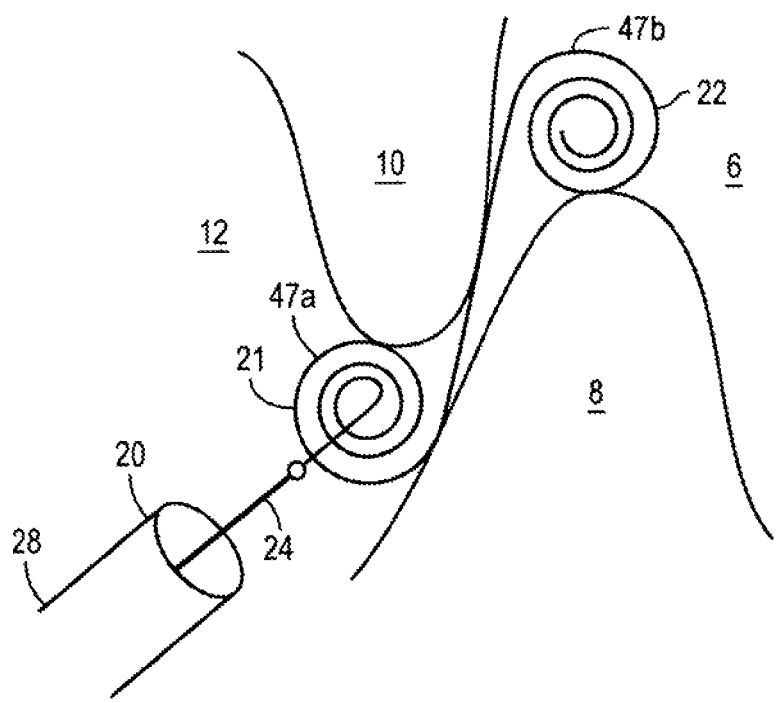
FIG. 9 depicts a side view of a coiled device for delivering energy to the left and right atrial sides an intracardiac defect according to an illustrative embodiment of the invention.

FIG. 9 depicts a side view of a coiled device for delivering energy to the left and right atrial sides an intracardiac defect according to illustrative embodiment of the invention. As shown in FIG. 9, in one embodiment, at least one coil 47a forms in the left atrium 6 and one coil 47b forms in the right atrium 12. For example, in one embodiment, the coil 47b forming in the left atrium 6 is formed from the same continuous wire that forms the coil 47a present in the right atrium 12. However, in a further embodiment, the coil 47b forming in the left atrium 6 is formed from a different wire than the wire from which the coil 47a in the right atrium 6 is formed. For example, in one embodiment, the system 18 comprises at least two energy delivery elements 22 contained within a delivery sheath 20 of a delivery catheter 28, one for deployment on the right atrial side 12 of the defect 14 and one for deployment on the left atrial side 6 of the defect.

In order to deploy the energy delivery element 22, an operator introduces the delivery catheter 28 into the left atrium 6 and retracts the delivery catheter proximally to allow coil 47a of the first energy delivery element 22 to deploy in the left atrium 6. The catheter 28 is then further retracted into the right atrium 12 to allow coil 47b of the second energy delivery element 22 to deploy in the right atrium 12. According to the invention, in one embodiment, the energy delivery element 22 is maintained in an uncoiled state within the delivery catheter 28 and when deployed from the delivery catheter 28, the energy delivery element 22 forms a coiled state. After deployment of the energy delivering element 22, energy is applied to the septum primum 8, septum secundum 10, and the tunnel 23, and the energy delivery element 22 is subsequently removed by recapture into the delivery catheter 28.

Figure 10:
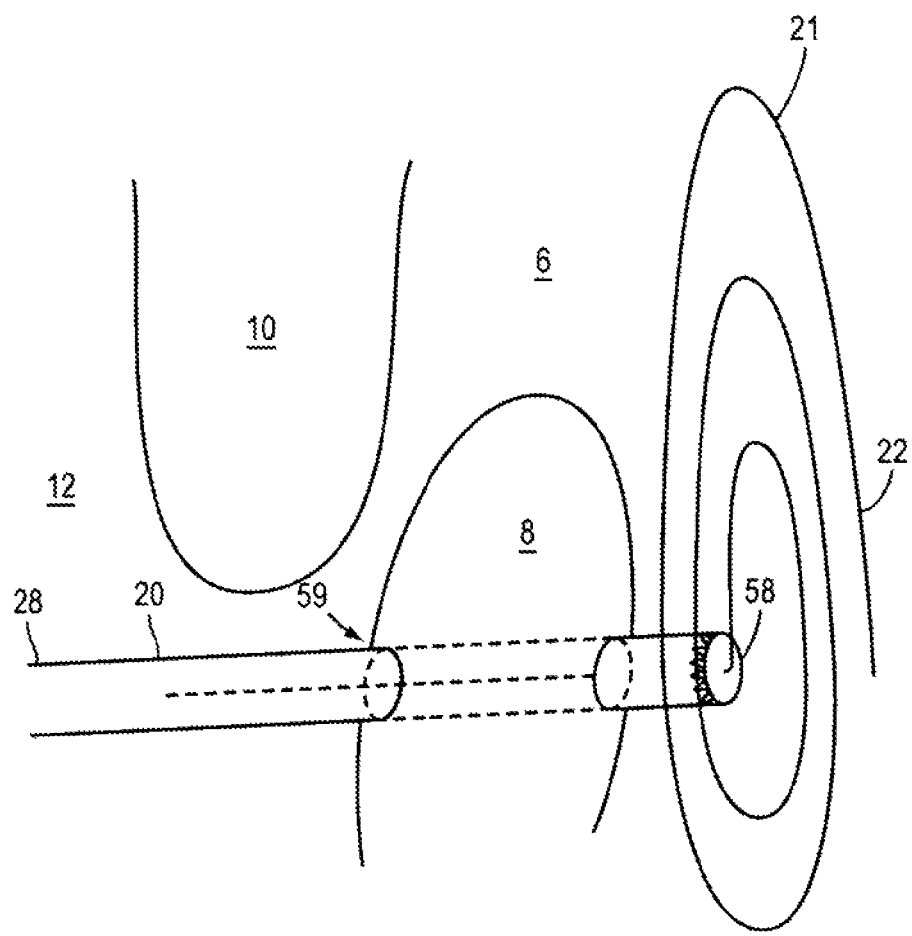
FIG. 10 depicts a method for delivering the device of FIG. 8 into an intracardiac defect via trans-septal puncture according to an illustrative embodiment of the invention.

FIG. 10 depicts a method for delivering the device illustrated in FIG. 8 into an intracardiac defect via trans-septal puncture according to an illustrative embodiment of the invention. The exemplary catheter 28 is introduced through the septum primum 8 into the left atrium 6. In one embodiment, the tip 58 of the catheter 28 is designed to puncture a hole 59 in the septum primum 8, allowing the catheter 28 to pass through. For example, the tip 58 of the catheter 28 is sharpened in one embodiment to permit puncturing of the septum primum 8. Once a hole is punctured in the septum primum 8, the delivery catheter 28 is moved distally into the left atrium 6 and is then retracted to allow one or more loops 21 of the energy delivery element 22 to deploy in the left atrium 6. The loops 21 of the energy delivery element 22 are pulled back distally against the septum primum 8 to appose the septum primum 8 to the septum secundum 10. Energy is delivered to the septum primum 8 and septum secundum 10 via the energy delivery element 22, and the energy delivery element 22 is then retracted through the hole 59 in the septum primum 8.

In another embodiment of a method for delivering the device of FIG. 8, the catheter 28 is introduced into the left atrial space 6 via trans-septal puncture of the septum secundum 10.

Figure 11:
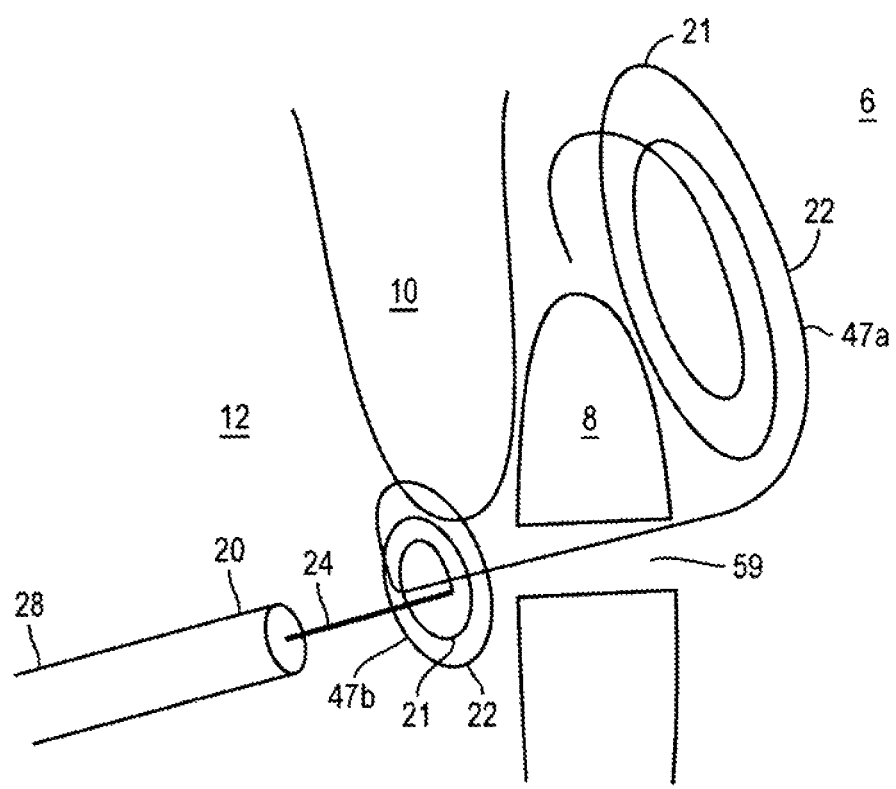
FIG. 11 depicts a method for delivering the device of FIG. 9 into an intracardiac defect via trans-septal puncture according to an illustrative embodiment of the invention.

FIG. 11 depicts a method for delivering the device illustrated FIG. 9 into an intracardiac defect via trans-septal puncture according to an illustrative embodiment of the invention. The exemplary delivery catheter 28 is introduced through a hole 59 in the septum primum 8 into the left atrium 6. In one embodiment, the tip 58 of the delivery catheter 28 is designed to puncture a hole 59 in the septum primum 8, allowing the delivery catheter 28 to pass through. For example, the tip 58 of the catheter 28 is sharpened in one embodiment. Once a hole 59 is punctured in the septum primum 8, the delivery catheter 28 is moved distally into the left atrium 6 and is then retracted proximally to allow the loops 21 of the first coil 47a of the energy delivery element 22 to deploy in the left atrium 6. The loops 21 of coil 47a are pulled back distally against the left atrial side of the septum primum 8 to appose the septum primum 8 to the septum secundum 10.

Next, the delivery catheter 28 is retracted into the right atrium 12 and the loops 21 of the second coil 47b of the energy delivery element 22 are deployed in the right atrium 12. In one embodiment, the loops 21 on the right atrial side 12 of the defect 14 appose the right atrial side of the septum primum 8 and septum secundum 10. Energy is delivered to the septum primum 8 and the septum secundum 10 via the energy delivery element 22, and the energy delivery element 22 is then recaptured by the catheter 28, with the portion of the energy delivery element 22 on the left atrial side 6 passing through the hole 59 in the septum primum 8. In another embodiment, the catheter 28 is instead introduced into the left atrial space 6 via a trans-septal puncture of the septum secundum 10.

Figure 12A:
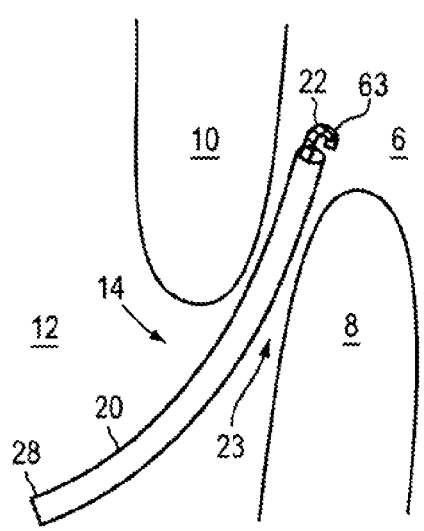
FIGS. 12A-D depict a hook-like electrode of an energy delivery element for delivering energy to an intracardiac defect according to an illustrative embodiment of the invention.

FIGS. 12A-D depicts an energy delivery element including a hook-like electrode for delivering energy to an intracardiac defect according to an illustrative embodiment of the invention. As shown in FIG. 12A, the energy delivery element 22 includes a hook-like electrode 63 retained within a delivery catheter 28 in a collapsed configuration. To deploy the energy delivery element 22, an operator advances the delivery catheter 28 into the left atrium 6 through the tunnel 23 of a patent foramen ovale 14. The energy delivering element 22 expands from its collapsed configuration to an expanded configuration once the operator retracts the delivery catheter 28 so that it no longer covers the energy delivery element 22. According to one embodiment, the energy delivery element 22 is maintained in a non-curved straight configuration within the catheter 28; however, when the energy delivery element 22 is deployed, the energy delivery element 22 forms a curvilinear configuration, for example, the hook shown in FIGS. 12A-D.

Figure 12B:
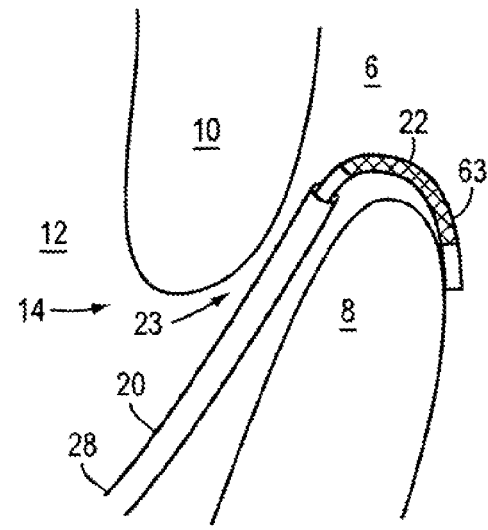
Figure 12C:
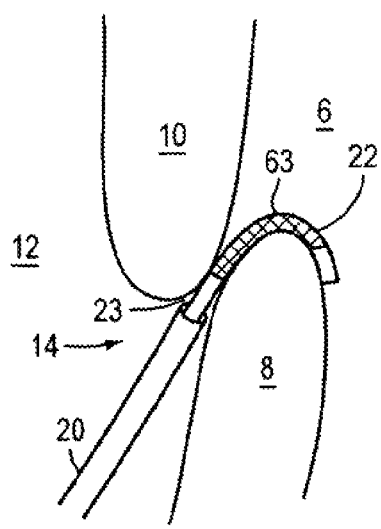
Figure 12D:
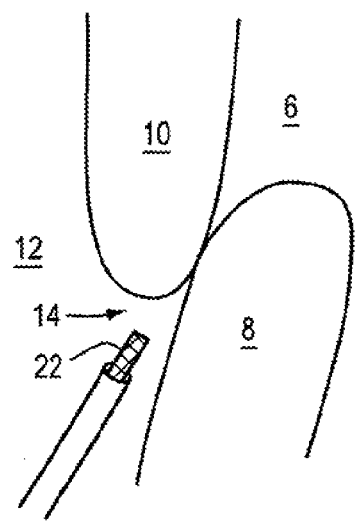

As shown in FIGS. 12B and 12C, the hook-like electrode 63 grasps the septum primum 8 and moves it closer to the septum secundum 10, as shown in FIG. 12C. Once the septum primum 8 and septum secundum 10 are properly apposed, energy is supplied through the energy delivery element 22 and the element 22 is removed, as shown in FIG. 12D, leaving the septum secundum 10 and septum primum 8 welded together.

In a further embodiment, in addition to an energy delivery element 22 including a hook-like electrode 63 as shown in FIG. 12A-D, a second energy delivery element (not shown) for apposing the septum primum 8 and septum secundum 10 on the right atrial side 12 of the patent foramen ovale 14 is included. The second energy delivery element 22 may be of any suitable shape such as, but not limited to, a disc, a ring, a square or a rectangle, which may be a solid body or as simple as a wire formed into the desired geometrical shape. The second energy delivery element is preferably made of a shape memory alloy, such as nitinol. In a further embodiment, the portion of the second energy delivery element contacting the blood of the right atrium 12 is coated with an insulating material.

After the hook-like electrode 63 of the energy delivery element 22 is deployed in the left atrium 6, the operator further retracts the delivery catheter 28 proximally into the right atrium 12 to deploy the second energy delivery element on the right atrial side 12 of the patent foramen ovale 14. In one embodiment, the second energy delivery element is continuous with the first energy delivery element 22, while in another embodiment, the second energy delivery element is a separate body from the first energy delivery element 22. With the second energy delivery element apposing the septum primum 8 and septum secundum 10 on the right atrial side 12 and the hook-like electrode 63 of the first energy delivery element 22 apposing the left atrial side 6 of the septum primum 8 against the septum secundum 19, the operator activates the energy source 26, delivering energy to the patent foramen ovale 14. The operator then removes the energy delivery elements 22 by retracting them into the delivery catheter 28.

Figure 13:
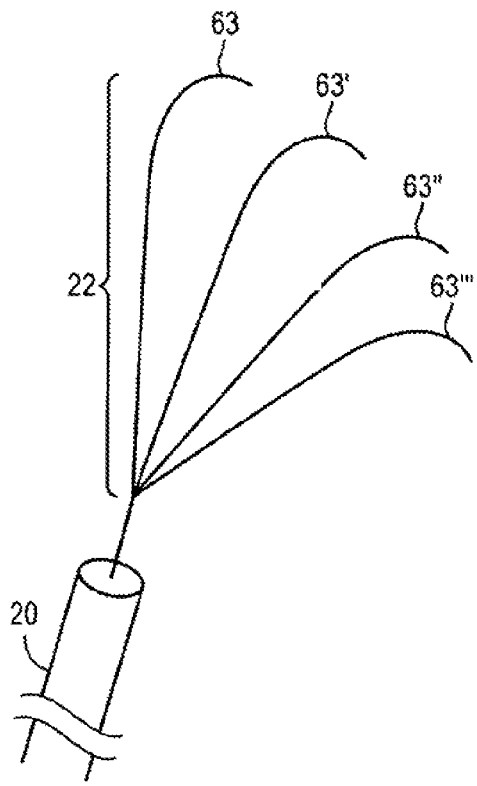
FIGS. 13-15 depict energy delivery elements including a plurality of hook-like electrodes illustrative of the invention.
Figure 14:
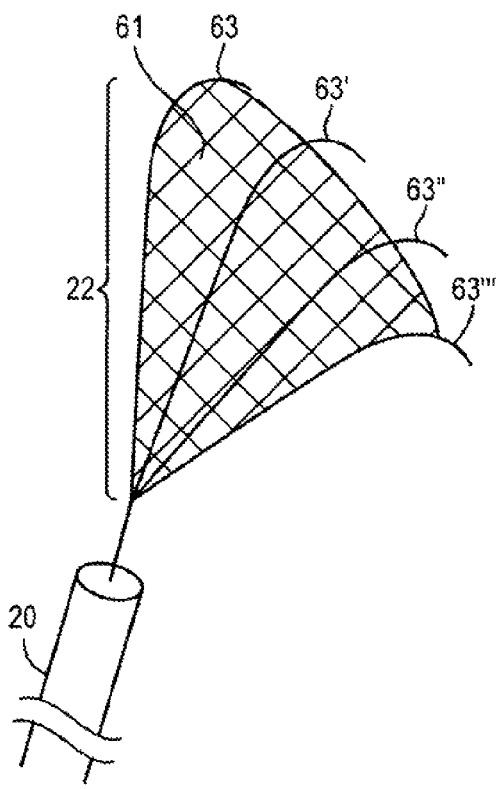
Figure 15:
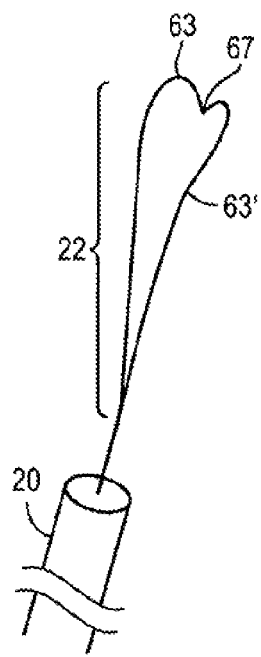

While the energy delivery element 22 of FIGS. 12A-D has only one hook-like electrode, FIGS. 13-15 depict energy delivery elements including a plurality of hook-like electrodes according to illustrative embodiments of the invention, which can be used in the same manner as the embodiment shown in FIGS. 12A-D for closing an intracardiac defect. As shown in FIG. 13, according to one embodiment, an energy delivery element 22 has more than one hook-like electrode 63. For example, an energy delivery element may have 1, 2, 3, 4, 5, 6, 7, 8, 9, 10 or more hook-like electrodes 63.

As shown in FIG. 14, in a further embodiment, the hook-like electrodes 63 act as a framework for a mesh-like fabric 61. The fabric 61 conducts energy and increases the surface area of energy delivery at the site of the intracardiac defect. The fabric can be composed of a metal, a polymer, a bioabsorbable material or any other suitable conductive material. In another embodiment, the hook-like electrodes 63 of the energy delivery element 22 are made of a shape-memory alloy such as nitinol. In a further embodiment, the hook-like electrodes 63 and/or the mesh structure 61 are coated with a non-stick coating, such as polytetrafluoroethylene (PTFE), to prevent the energy delivery element 22 from adhering to the septum primum 8 and septum secundum 10 after energy is introduced. Alternatively, as shown in FIG. 15, in another embodiment, the tips or ends 67 of two hook-like electrodes 63 are joined to create a continuous loop.

Similar to the multi-hook energy delivery elements of FIGS. 13-15, FIGS. 16A-B depict a system for delivering energy to an intracardiac defect. The system includes an energy delivery element with multiple hook-shaped electrodes and an intracardiac occluder according to an illustrative embodiment of the invention. An intracardiac occluder 66 comprises generally a framework formed by a plurality of elongated struts 71 which radiate from a central hub 68, according to one embodiment of the invention. Elongated struts 71, in one embodiment, have points 78 where energy delivery is concentrated.

An intracardiac occluder 66 has one occlusion shell 62 in one embodiment, while in another embodiment, the intracardiac occluder 66 has two or more occlusion shells 62a, 62b (collectively 62). For example, the framework 71 extending on a first side of the central hub 68 is a first occlusion shell 62a, while the framework 71 extending on an opposite second side of the central hub 68 is a second occlusion shell 62b. Alternatively, attached to the strut frameworks 71 are patches 65a, 65b (collectively 65) which, when the occluder 66 is deployed, cover and occlude the patent foramen ovale 14.

Figure 16A:
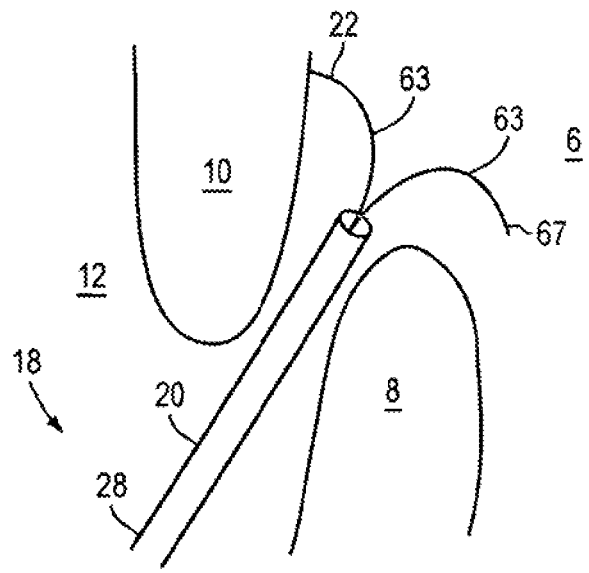
FIGS. 16A-B depict a system for delivering energy to an intracardiac defect including a multi-hook energy delivery element and an intracardiac occluder according to an illustrative embodiment of the invention.

As shown in FIG. 16A, the system 18 includes a delivery catheter 28 with a sheath 20 that is retracted to deploy the energy delivery element 22. In one embodiment, the energy delivery element 22 consists of two hook-like electrodes 63. In a further embodiment, the energy delivery element has three or more hook-like electrodes 63. In a further embodiment, the curve of the hook-like electrodes 63 passes through more than one plane. In a further embodiment, the curve of the hook-like electrodes 63 is in the same plane. In another embodiment, the hook-like structures 63 exhibit a curve including a free end 67.

Figure 16B:
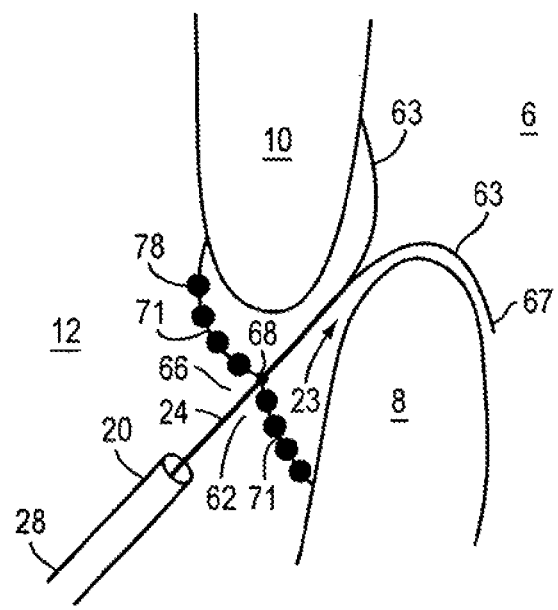

As shown in FIG. 16B, in one embodiment, the energy delivery element 22, in addition to including a plurality of hook-like electrodes 63, also includes an occlusion shell 62. In one embodiment, an occluder 66 including only one occlusion shell 62 is positioned at the distal end of the cable 24, while in another embodiment, an occluder 66 including two occlusion shells 62a, 62b is positioned at the distal end of the cable 24.

FIGS. 16A-B show two stages of deployment of an energy delivery element including two hook-like electrodes and an occlusion shell of an intracardiac occluder. As shown in FIG. 16A, the operator advances the delivery catheter 28 into the right atrium 12. The operator then retracts the catheter 28 to uncover the hook-like electrodes 63 which deploy in the left atrium 6. The operator then moves the catheter 28 proximally into the right atrium 12 causing the hook-like electrodes 63 to bring the septum primum 8 and septum secundum 10 into apposition. The occluder 66 of the energy delivery element 22 is next deployed in the right atrium 12.

As shown in FIG. 16B, in one embodiment, the occluder 66 of the energy delivery element 22 has only one occlusion shell 62. To deploy the occlusion shell 62 of the energy delivery element 22, after the operator moves the catheter 28 proximally into the right atrium 12, as described above, the operator further retracts the catheter 28 to deploy the occlusion shell 62 of the occluder 66. In one embodiment, the occlusion shell 62 of the energy delivery element 22 apposes the septum primum 8 and septum secundum 10 on the right atrial side 12 of the defect 14.

Alternatively, in another embodiment, the occluder 66 has two occlusion shells 62, as discussed below in relation to FIGS. 17A-B. The distal occlusion shell 62b is first deployed in the left atrium 6 by retracting the delivery catheter 28 proximally. The catheter is then withdrawn into the right atrium 12 to deploy the proximal occlusion shell 62a. In another embodiment, a distal occlusion shell 62b is deployed in the left atrium 6 simultaneously with or after the deployment of the hook-like electrodes 63. The catheter 28 is then further retracted into the right atrium 12 to subsequently deploy the proximal occlusion shell 62a.

In one embodiment, the occlusion shell 62 is an embodiment described in U.S. Pat. No. 5,425,744, the entire disclosure of which is incorporated by reference herein. In another embodiment, the occlusion shell 62 is an embodiment described in U.S. Pat. No. 5,451,235, the entire disclosure of which is incorporated by reference herein. In yet another embodiment, the occlusion shell 62 is an embodiment described in U.S. Pat. No. 5,709,707, the entire disclosure of which is incorporated by reference herein.

In one embodiment, the occlusion shell 62 assists in the apposition of the septum primum 8 and the septum secundum 10. In another embodiment, the occlusion shell 62 may also act as an electrode for the delivery of energy to the septum primum 8 and the septum secundum 10 of the patent foramen ovale 14. After the energy delivery element 22 and the occlusion shell 62 are appropriately positioned, energy is delivered to the septum primum 8 and septum secundum 10, and the tunnel 23 of the patent foramen ovale 14, welding the septum primum 8 and the septum secundum 10 together. In one embodiment, the energy delivery element 22 and occlusion shell or shells 62 are then removed and the intracardiac defect is allowed to heal. In another embodiment, the hook-like electrodes 63 are removed, while the occlusion shell or shells 62 remain implanted at the site of the patent foramen ovale 14.

Figure 17A:
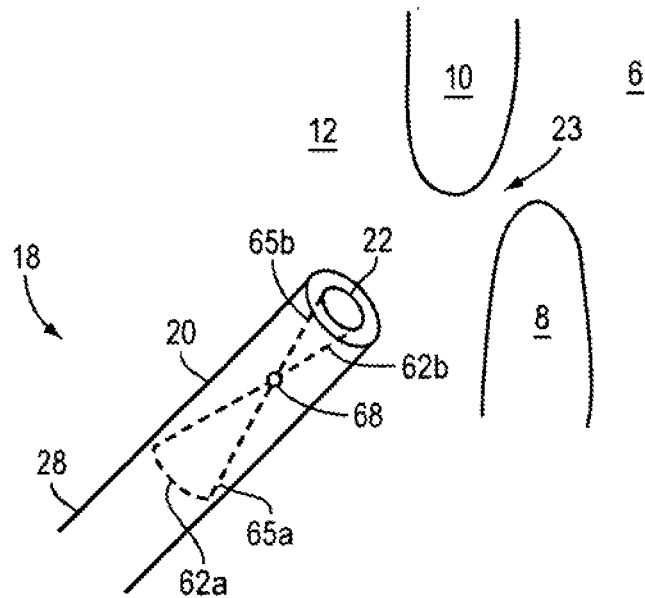
FIGS. 17A-C depict a system for delivering energy to an intracardiac defect including an energy delivery element with two occlusion shells according to an illustrative embodiment of the invention.
Figure 17B:
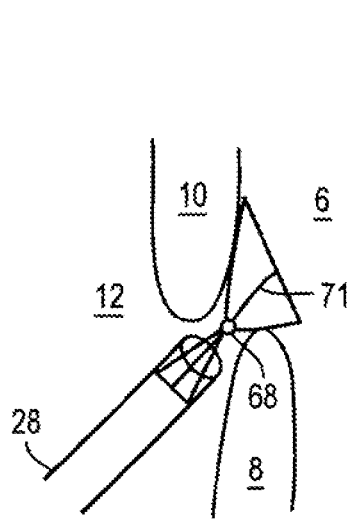
Figure 17C:
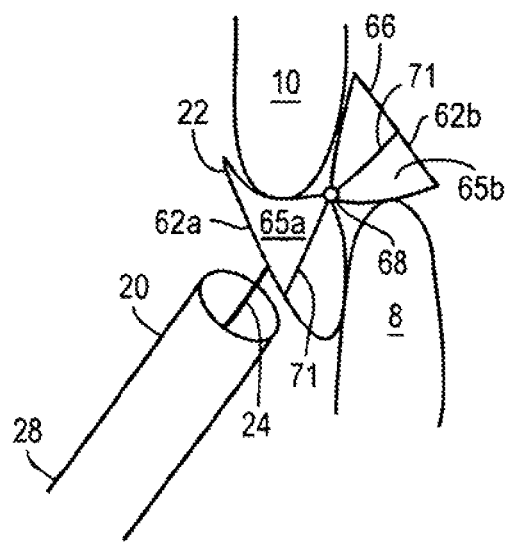

FIGS. 17A-C depict a system for delivering energy to an intracardiac defect including an energy delivery element with two occlusion shells, according to an illustrative embodiment of the invention. For example, in one embodiment, one occlusion shell is a proximal occlusion shell 62 while the other occlusion shell is a distal occlusion shell. In a further embodiment, one occlusion shell is connected to the second occlusion shell via a central hub 68. As shown in FIG. 17A, a catheter 28 including a sheath 20 encloses the energy delivery element 22 which in one embodiment includes two occlusion shells 62a, 62b. In a further embodiment, the energy delivery element 22 includes at least one hook-like electrode 63 and two occlusion shells 62a, 62b.

The occluder 66 is connected permanently to the distal end 27 of the cable 24 in one embodiment, while in another embodiment, the occluder 66 is connected releasably to the distal end 27 of the cable 24. For example, in one embodiment, the occluder 66 is attached to the cable 24 via an attachment device. A non-exhaustive list of attachment devices include a ball-rod connection, a ball-socket connection, a ball-claw connection, a threaded connection, a looped connection, a magnetic connection, a male-female connection, an adhesive connection, a clamped connection, and a hook-eye connection. In a further embodiment, the attachment device is insulated, for example by a coating or sleeve of non-conductive material.

In one embodiment, at least one of the occlusion shells 62 includes a plurality of struts 71 which radiate from the central hub 68, with each strut including one flexural point (not shown) about which the strut may flex. In a further embodiment, a first strut 71 from a first occlusion shell 62a is connected with a first strut of a second occlusion shell 62b via a centering mechanism. In another embodiment, a first strut 71 of a first occlusion shell 62a is connected to a first strut 71 of a second occlusion shell 62b, and a second strut 71 of a first occlusion shell 62a is connected to a second strut 71 of a second occlusion shell 62b. For example, in one embodiment the connection is formed by an elastomeric material.

The strut framework 71 of one or more occlusion shells 62 is covered with a biocompatible or bioabsorbable patch 65a, 65b (collectively 65), as disclosed in U.S. Pat. No. 5,425,744. Other types of occlusion shells, e.g., those disclosed in U.S. Pat. No. 5,425,744, 5,451,235, or 5,709,707 may also be used. In one embodiment, the patch 65 includes a conductive material such as metal, for example, a metal mesh, or a conductive polymer to enhance the delivery of energy to the intracardiac defect. In a further embodiment, the patch 65 includes one or both of an adhesive or growth stimulating substance that is deposited on the septum primum 8 and septum secundum 10 of the patent foramen ovale 14 to enhance defect closure. In a further embodiment, the patch 65 includes a biological material such as collagen or submucosa.

In another embodiment, the arms or struts 71 of the occlusion shell 62 include a coil, such as for example, a helically curved strut or a spiral strut 71. According to one embodiment, the occlusion shell 62 has any number of arms or struts 71.

In order to deliver the energy delivery element 22 including the occluder 66 to the patent foramen ovale 14, the catheter 28 is inserted into the left atrium 6 through the tunnel 23 of the patent foramen ovale 14. As shown in FIG. 17B, the delivery catheter 28 is then retracted proximally to deploy the distal occlusion shell 62 which apposes the tissues of the septum primum 8 and the septum secundum 10 on the left atrial side 6. The catheter 28 is then drawn further proximally into the right atrium 12 to deploy the proximal occlusion shell 62a of the energy delivery element 22, as shown in FIG. 17C. Energy is delivered to the energy delivery element including the occluder 66, and in one embodiment, the energy delivery element including the occluder 66 is withdrawn from the patient, while in another embodiment, the occluder 66 remains implanted at the site of the patent foramen ovale 14, i.e., the occluder 66 is detached from cable 24.

In one embodiment, the occlusion shell 62 assists in apposing the septum primum 8 and the septum secundum 10. In another embodiment, the occlusion shells 62a, 62b act as electrodes for the delivery of energy to the septum primum 8 and the septum secundum 10 of the patent foramen ovale 14. After energy is delivery to the septum primum 8, the septum secundum 10, and the tunnel 13 of the patent foramen ovale 14, the septum primum 8 and the septum secundum 10 weld together, according to one embodiment of the invention. In a further embodiment, any hook-like electrode 63 is removed from the patent foramen ovale 14, while the occlusion shell or shells 62 remain implanted at the site of the patent foramen ovale 14.

Figure 18:
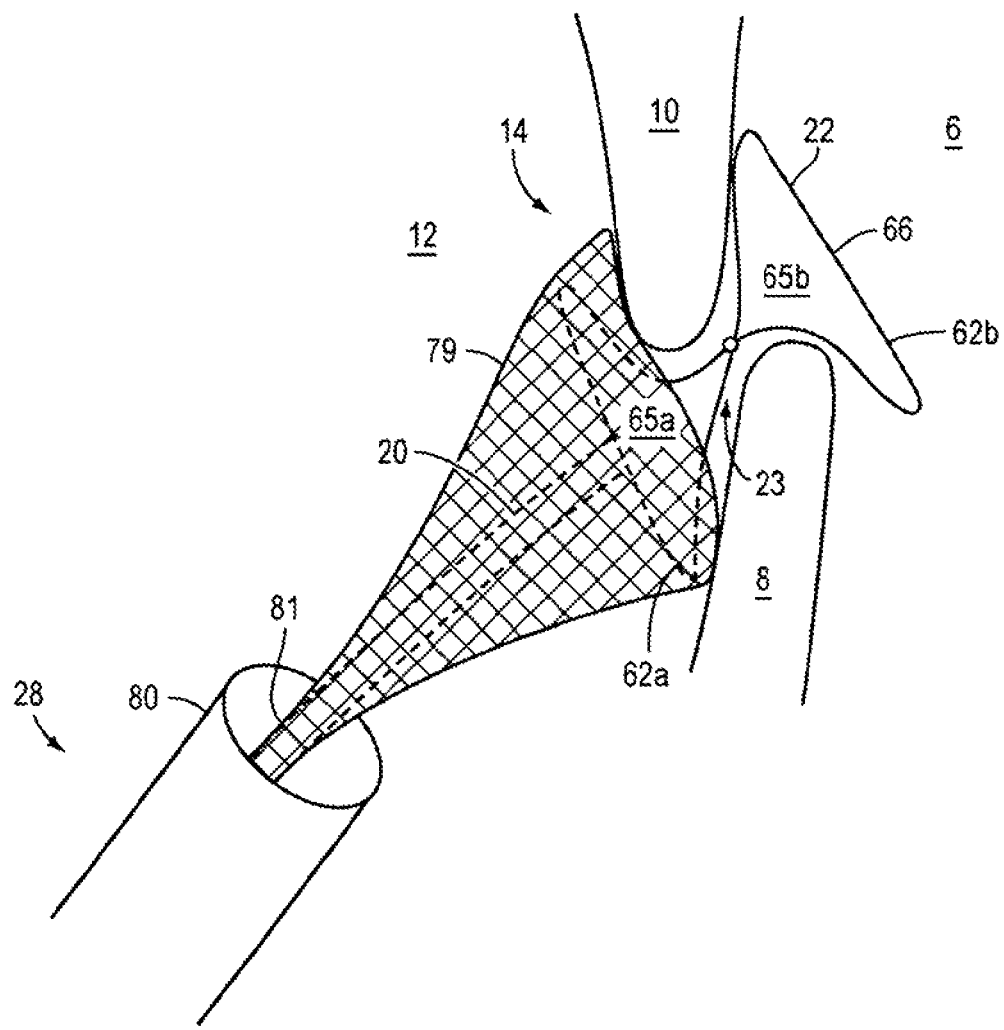
FIG. 18 depicts a side-view of a system for delivering energy to an intracardiac defect including a vacuum apparatus and an energy delivery element including an intracardiac occluder according to an illustrative embodiment of the invention.

FIG. 18 depicts a side-view of a system for delivering energy to an intracardiac defect including a vacuum apparatus and an energy delivery element including an intracardiac occluder according to an illustrative embodiment of the invention. According to the invention, a catheter 80, capable of providing negative pressure, i.e., a vacuum, is included in the system 18 for delivering energy to an intracardiac defect. While the vacuum catheter 80 described herein may be utilized with any of the embodiments of the energy delivery elements 22 disclosed herein, the vacuum catheter 80 is described in conjunction with an energy delivery element 22 including an occluder 66.

As shown in FIG. 18, an energy delivery element 22, such as an intracardiac occluder 66 including a pair of occlusion shells 62 is attached either permanently or releasably to the cable 24 of the catheter 80. The catheter 80 is operatively connected to a vacuum force producing source (not shown). The vacuum is created by the source (not shown) and applied to the patent foramen ovale 14 via the vacuum force containing element 79. The distal end of the vacuum force containing element 79, in one embodiment is shaped like a cone, while in another embodiment is shaped like a cup. Any suitable geometrical shape for the force containing element 79 can be used, so long as it will allow apposition between the force containing element and the patent foramen ovale 14.

With continued reference to FIG. 18, extending proximally from the distal end of the vacuum force containing element 79 is a tube 81 that connects the distal end of the vacuum force containing element 79 to the vacuum force producing source (not shown). The vacuum force containing element 79, in one embodiment, is made of a fabric, while in another embodiment, it is made of a metal such as a shape memory alloy. In a further embodiment, the fabric is supported by a metal frame, preferably collapsible and made of a shape memory alloy, such that the vacuum force containing element 79 is retained inside the catheter 28 in collapsed configuration prior to deployment can expand upon retraction of the catheter 28 for deployment.

In order to deploy the energy delivery element 22 at the site of the patent foramen ovale 14, the operator introduces the catheter 80 housing the vacuum force containing element 79 and the energy delivery element 22 into the left atrium 6. As shown in FIG. 18, the energy delivery element 22 in one exemplary embodiment includes two occlusion shells. The operator retracts the catheter 28 proximally to deploy the distal occlusion shell 62. The catheter 28 is then further retracted proximally to deploy the proximal occlusion shell 62a and the vacuum force containing element 79. After deployment, the vacuum force containing element 79 abuts the right atrial wall of the septum primum 8 and the septum secundum 10 (the area known as the fossa ovalis), and the operator then enables the vacuum force producing source.

The vacuum force is strong enough to remove any debris from the area and causes the septum primum 8 and septum secundum 10 to come together, closing the tunnel 23. The energy delivery element 22 delivers energy to the patent foramen ovale 14 at any point before, during or after the application of the vacuum force. In one embodiment, once the energy has been delivered and the vacuum force applied, both the vacuum force containing element 79 and the occlusion shells 62 are retracted from the patent foramen ovale 14. In another embodiment, the vacuum force containing element 79 is removed and the occlusion shells 62 of the occluder 66 remain permanently implanted at the site of the patent foramen ovale 14.

Figure 19A:
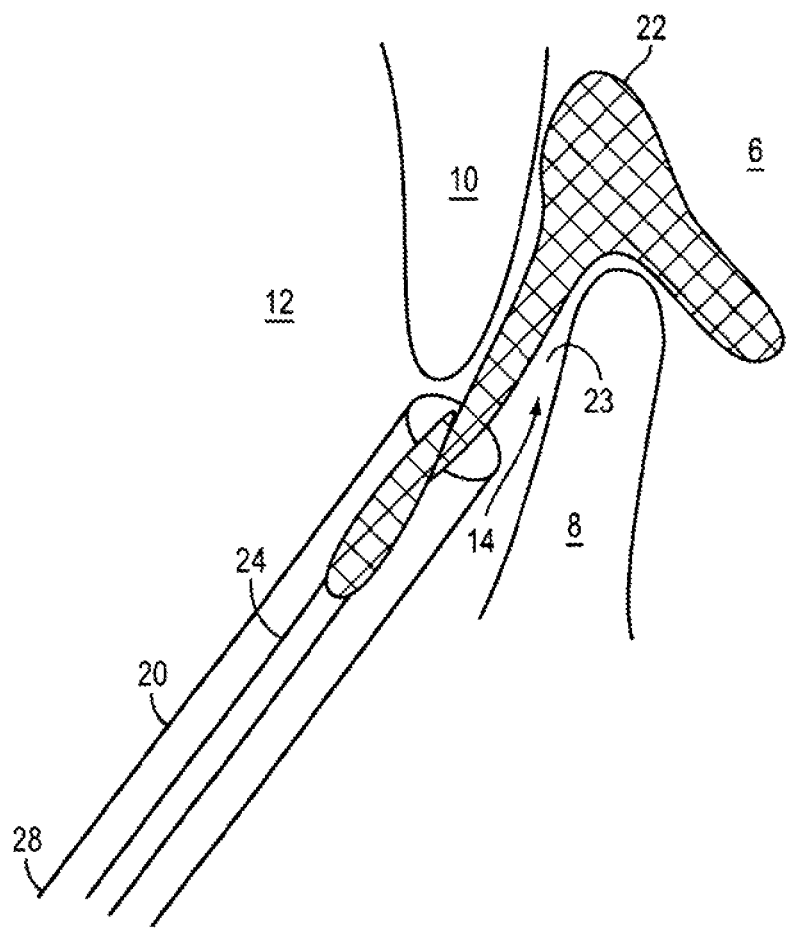
FIGS. 19A-B depict a side view of a system for delivering energy to an intracardiac defect including a braided energy delivery element, according to an illustrative embodiment of the invention.
Figure 19B:
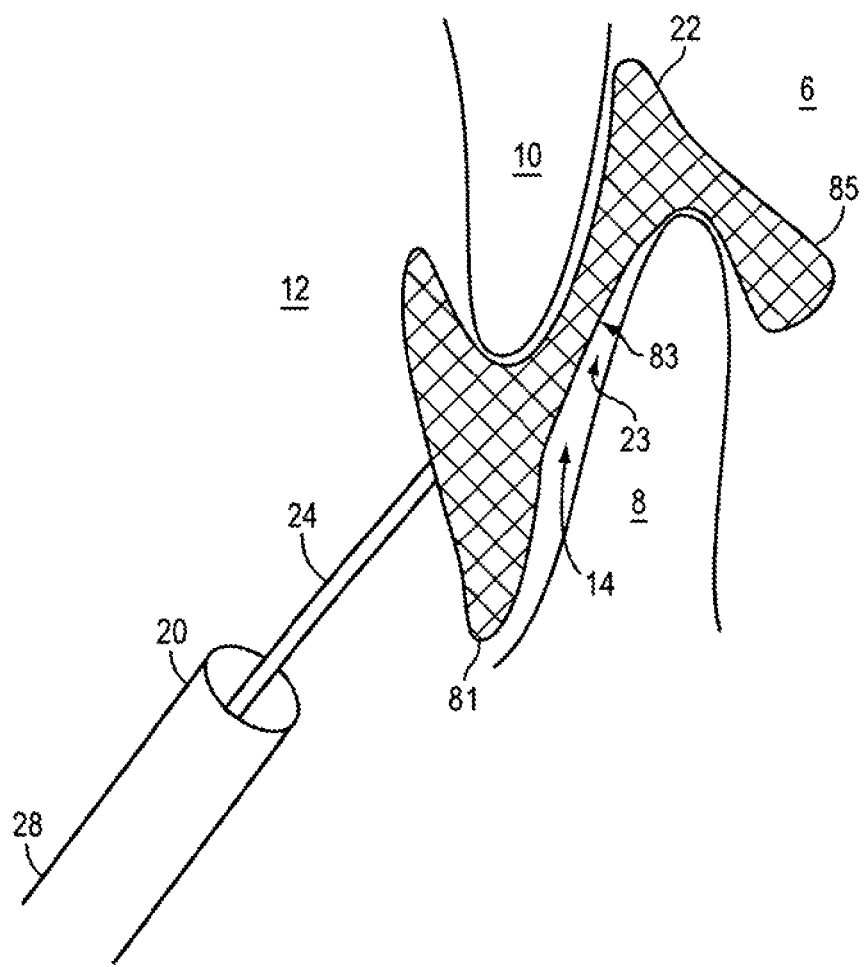

FIGS. 19A-B depict a side view of a system for delivering energy to an intracardiac defect including a braided energy delivery element, according to an illustrative embodiment of the invention. As shown in FIG. 19B, the braided energy delivery element 22 comprises a proximal section 81 for occluding the right atrial side 12 of the patent foramen ovale 14, a middle section 83 for occluding the tunnel 23, and a distal section 85 for occluding the left atrial side 6 of the patent foramen ovale 14. According to one embodiment, the braided energy delivery element 22 comprises an "H" shape.

The braided energy delivery element 22, according to one embodiment of the invention, is connected at its proximal section to cable 24. Cable 24 is connected to an actuating mechanism (not shown). In order to move the braided energy delivery element 22, an operator moves the actuating member proximally to move the energy delivery element 22 proximally, while the operator moves the actuating member distally to move the energy delivery element 22 distally.

In a further embodiment, the distal 85, middle 83 and proximal 81 sections of the braided energy delivery device 22 are composed of a braided material, such as a woven, plaited, or mesh fabric. According to one embodiment, the mesh may be made of any suitable metal such as, but not limited to, stainless steel or a shape memory alloy such as nitinol. Alternatively, the mesh may be made of a conductive polymer or other conductive material that can be woven into a mesh-like structure. For example, the distal 81, middle 83, and proximal 85 sections in one embodiment are composed of one contiguous piece of wire mesh.

In another embodiment, the braided energy delivery element 22 comprises a distal section 81, a middle section 83, and a proximal section 85 wherein each section is a separate component joined together, for example by a joining piece such as a hinge (not shown). In yet another embodiment, the joining piece, such as a hinge, is activated by energy causing the distal 85 and proximal 81 sections of braided material to clamp the septum primum 8 and septum secundum 10, apposing those tissues.

In another embodiment, one or more of the proximal 81, distal 85 and middle 83 sections may include one or more non-braided portions. For example, the proximal section 81 and the distal section 85 of the energy delivery element in one embodiment are composed of a braided material, while the middle section 83 is made of a solid piece of metal or other conductive material. In an alternate embodiment, the proximal and distal sections 81, 85 are composed of a braided material, while the middle section 83 includes a braided portion and a non-braided portion, i.e., a solid piece of metal.

In a further embodiment, the braided energy delivery element or at least one or more of the proximal 81, distal 85, or middle section 83 is coated with one or more of an adhesive, a bioabsorbable material, a metal of low melting point, a polymer, or a growth stimulating substance. The coating is released from the energy delivery element 22 and deposited at the patent foramen ovale before, during or after application of the energy to assist in the closure of the patent foramen ovale 14.

The braided energy delivery element 22 is delivered to the patent foramen ovale 14 via a catheter 28 which maintains the energy delivery element 22 in a compressed configuration until the operator retracts the catheter 28 proximally to deploy the energy delivery element 22. As shown in FIG. 19B, the braided energy delivery element 22, when deployed, is positioned to occlude the patent foramen ovale 14 on the left atrial side 6, through the tunnel 23, and on the right atrial side 12. After delivery of energy to the patent foramen ovale 14, the energy delivery element 22 is collapsed into the catheter 28 and removed. Because the braided device 22 is extremely flexible, it is easily collapsed and recovered into the catheter 28 for removal.

Figure 20:
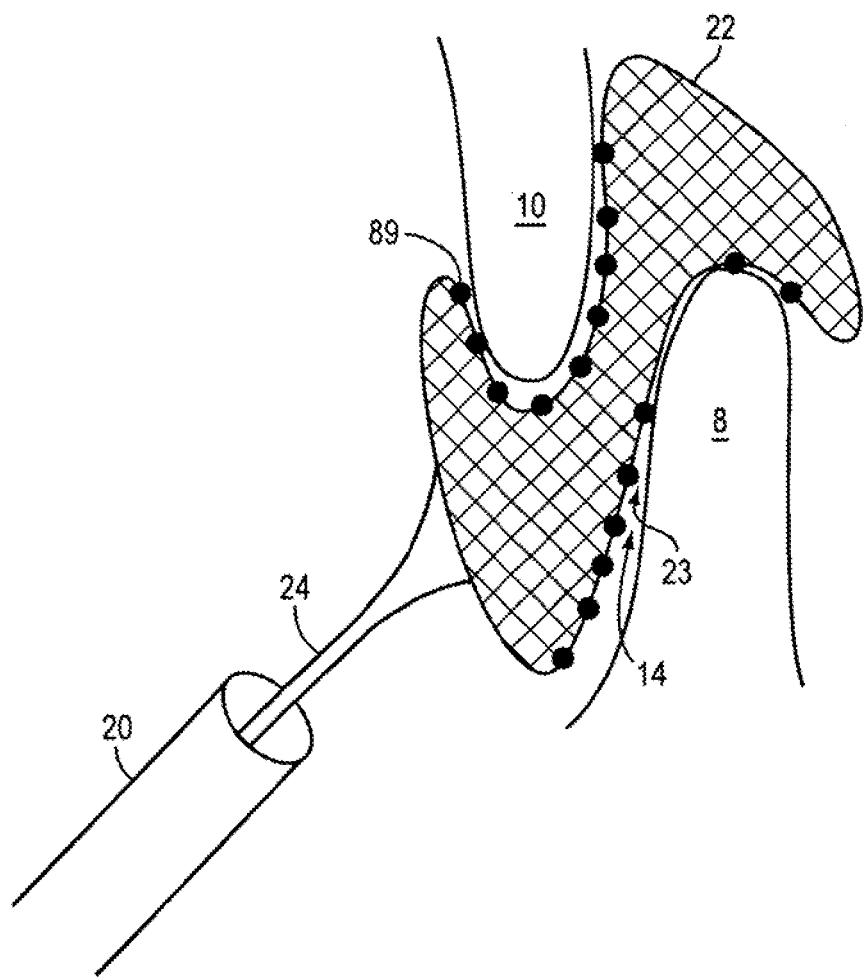
FIG. 20 depicts a braided energy delivery element with nodes on the surface for focusing energy delivery, according to an illustrative embodiment of the invention.

Another advantage of using a braided energy delivery element 22 includes the ability to deliver energy over the entire element 22 or to only deliver energy to one or more specific sites on the braid 22. For example, FIG. 20 depicts a braided energy delivery element 22 with nodes on the surface for focusing energy delivery, according to an illustrative embodiment of the invention. As shown in FIG. 20, energy is delivered to point locations 89 on the energy delivery element 22 to concentrate the delivery of energy to the surface of the septum primum 8 and the septum secundum 10, as well as the tunnel 23 of the patent foramen ovale 14.

In another embodiment, (not shown) energy is delivered along one or more linear pathways of the braided energy delivery element 22. Alternatively, energy may be delivered along a broken pathway of the braided energy delivery element 22. In another embodiment, energy can be delivered in geometric pattern such as a circular, square shaped or oval shaped pathway; however, any suitable geometric pathway may be used. In another embodiment, portions of the braided energy delivery element 22 are insulated with a sleeve or coating of a non-conductive material to facilitate the concentration of energy delivery at a point location, or along a linear, geometric or broken pathway.

Figure 21A:
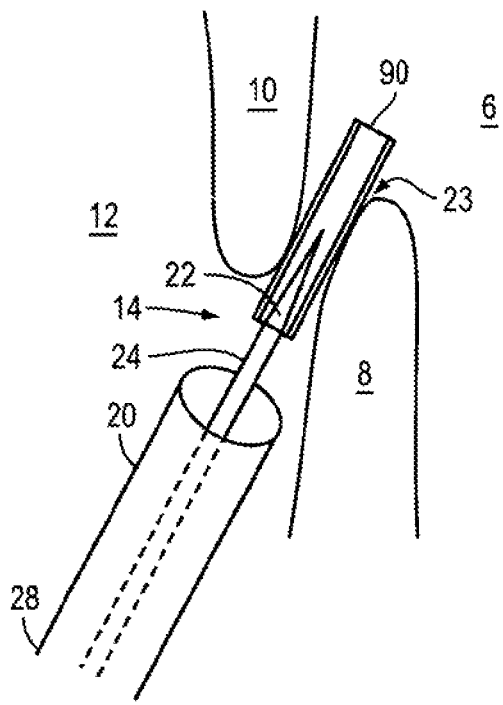
FIGS. 21A-B depict a perspective view of a system for delivering energy to an intracardiac defect including a plug for occluding the defect according to an illustrative embodiment of the invention.
Figure 21B:
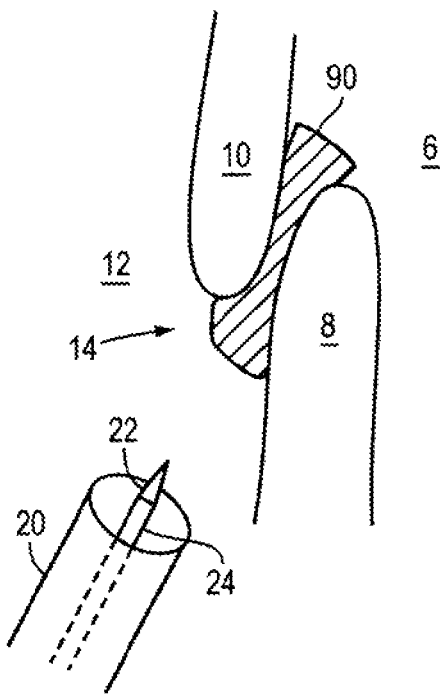

FIGS. 21A-B depict a perspective view of a system for delivering energy to an intracardiac defect including a plug for occluding the defect according to an illustrative embodiment of the invention. The plug 90 is positioned at the distal end of the cable 24 of the delivery catheter 28. The plug 90 is shaped like a cylinder in one embodiment, while in another embodiment, the plug 90 is shaped like a cone. An energy delivery element 22 is also positioned at the distal end of the cable 24.

As shown in FIG. 21, the energy delivery element 22 is positioned within the plug 90, according to one embodiment. However, in an alternate embodiment, the plug 90 is contained within the energy delivery element 22. For example, in one embodiment, the energy delivery element 22 includes a metal wire or mesh fabric container (not shown) at the distal end of the cable 24 that houses the plug 90 and can be withdrawn proximally from the plug 90 after delivering energy, leaving the plug 90 in the tunnel 23 of the patent foramen ovale 14.

In a further embodiment, the plug 90 expands to occlude the tunnel 23 when energy is applied. As shown in FIG. 21B, upon application of energy, the plug 90 adheres to the septum primum 8 and septum secundum 10 of the patent foramen ovale 14, allowing the energy delivery element 22 to be retracted without dislodging the plug 90. Furthermore, the plug 90 described herein can also be used in conjunction with any of the energy delivery elements 22 described herein.

In one embodiment, the plug 90 includes a bioabsorbable material such as tissue, preferably human tissue. In another embodiment, the plug 90 includes a polymer that upon application of energy, expands to fill the defect. In yet another embodiment, the plug 90 includes a shape memory alloy material that expands upon application of energy, and the plug 90, itself, acts as an energy delivery element 22. For example, in one embodiment, the shape memory alloy is nitinol. In a further embodiment, a plug 90 including a shape memory alloy delivers energy to a point or points on the plug 90, along one or more linear pathways, or to the entire plug 90.

In a further embodiment the plug 90 is permanently implanted into the tunnel 23 of the patent foramen ovale 14, while in another embodiment, the plug 90 is removable.

In a further embodiment, the plug 90 is encompassed by a sleeve or coating. For example, the sleeve or coating may include an adhesive, a bioabsorbable material, a polymer, a growth promoting substance, collagen, or a metal with a low melting point. According to one embodiment of the invention, the sleeve or coating is deposited in the patent foramen ovale 14 along with plug 90.

As shown in FIG. 21A, the plug 90 is introduced into the tunnel 23 of a patent foramen ovale 14 by a catheter 28. The plug 90 is maintained at the distal end of the delivery catheter 28. When the catheter 28 is positioned in the tunnel 23, the delivery catheter 28 is retracted to reveal the plug 90. Energy is applied, the plug 90 expands, and the catheter 28 and energy delivery element 22 are removed, leaving the plug 90 to occlude the patent foramen ovale 14.

Figure 22:
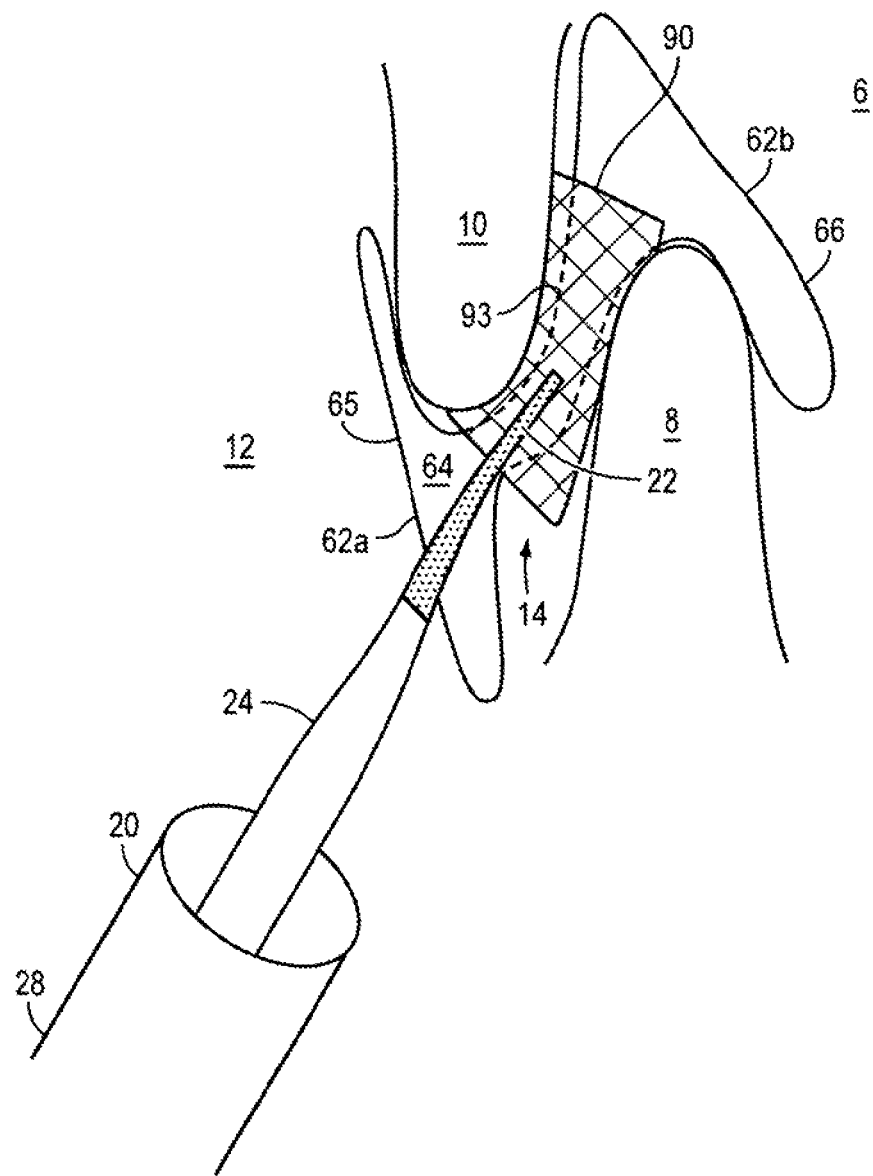
FIG. 22 depicts the device of FIG. 21 further including an intracardiac occluder, according to an illustrative embodiment of the invention.

FIG. 22 depicts the device of FIG. 21 further including an intracardiac occluder, according to an illustrative embodiment of the invention. As shown in FIG. 21, a plug 90 is positioned on the distal end of the cable 24. An intracardiac occluder 66 is also positioned on the distal end of the cable 24. In one embodiment, the intracardiac occluder 66 is an energy delivery element 22. In another embodiment, the cable further includes an energy delivery element 22 for delivering energy to the plug 90.

The plug 90 is introduced into the tunnel 23 of a patent foramen ovale 14, along with an intracardiac occluder 66, according to methods previously described herein. In one embodiment, the plug 90 is coaxial with the middle section 93 of the occluder 66, while in another embodiment, the plug 90 is adjacent to the middle section 93 of the occluder 66. In one embodiment, the occluder 66 includes two occlusion shells 62 with the proximal occlusion shell 62a being deployed in the right atrium 12 and the distal occlusion shell 62b being deployed in the left atrium 6 according to methods previously disclosed herein. The occluder 66 may be of any suitable geometry, such as, but not limited to a spiral shaped occluder, an umbrella shaped occluder, a petal shaped occluder, or a flat monolithic body, or any other type of occluder, e.g., those disclosed in U.S. Pat. No. 5,425,744, 5,451,235, or 5,709,707. In one embodiment, the occluder 66 is a bioabsorbable occluder.

All the embodiments of energy delivery elements 22 described herein can include a coating or sleeve on the energy delivery element 22 which bonds to the septum primum 8 and septum secundum 10 of the patent foramen ovale 14. The sleeve or coating may be made from one or more bioresorbable materials, adhesives, polymers, or metals, and maybe include growth stimulating substances. According to one embodiment, when the energy delivery element 22 is withdrawn from the patent foramen ovale 14, the coating or sleeve remains at the site of the defect 14, improving closure of the tunnel 23.

Furthermore, the invention described herein contemplates that all embodiments of the energy delivery elements 22 disclosed herein can be delivered to the site of an intracardiac defect 14 such as a patent foramen ovale 14 in conjunction with a vacuum catheter system 80 as described herein.

In addition, all energy delivery elements 22 disclosed herein, can be made of a shape memory alloy, such as nitinol. Because shape memory properties of a metal are activated by changes in temperature of the metal, the various energy delivery elements 22 described herein can thus be designed to provide a temporary clamping force on the septum primum 8 and septum secundum 10 when energy is applied.

Moreover, because applying energy causes coagulation of the tissue, all energy delivery elements 22 disclosed herein can be coated with a non-stick surface such as polytetrafluoroethylene (PTFE) to ease removal of the energy delivery element 22 from the patent foramen ovale 14.

In addition, any of the embodiments herein are useful for closing any intracardiac defect, such as an atrial septal defect, a ventricular septal defect, and for obliteration of a left atrial appendage.

Variations, modifications, and other implementations of what is described herein will occur to those of ordinary skill in the art without departing from the spirit and scope of the invention as claimed. Accordingly, the invention is to be defined not by the preceding illustrative description alone, but by the spirit and scope of the following claims.

The invention claimed is:

1. A medical device for occluding the tunnel of a patent foramen ovale (PFO) in a patient comprising: an occluding member, a sheath comprising a lumen; an elongated member, one of said elongated member and said sheath axially moveable relative to the other; and an energy delivering element comprising a plug comprising animal tissue and joined to said elongated member, wherein said plug comprises a core member sized and shaped to substantially fill the tunnel of the PFO, and wherein further the occluding member comprises a proximal occluder including a plurality of outwardly extending proximal arms supporting a proximal occlusion shell and a distal occluder including a plurality of outwardly extending distal arms supporting a distal occlusion shell and a centering mechanism secured between said proximal occluder and said distal occluder to center said proximal and said distal occluders about a defect, said centering mechanism comprising at least two centering members, each of said centering members secured between a separate one of said proximal arms and a corresponding one of said distal arms, at least one of said centering members comprising an elastomeric material.

2. The device of claim 1, wherein said plug comprises a resorbable material.

3. The device of claim 1, wherein said plug is expandable.

4. The device of claim 3, wherein said plug is expandable upon application of energy to the plug.

5. The device of claim 1, wherein the energy delivering element delivers RF energy.

6. The device of claim 5, wherein the RF energy is supplied to one or more points on said plug.

7. The device of claim 5, wherein the RF energy is supplied along one or more linear pathways of the plug.

8. The device of claim 5, wherein the RF energy is supplied to the entire plug.

9. The device of claim 1, wherein the occluding member comprises a bioabsorbable material.

10. The device of claim 1, wherein the plug further comprises a sleeve or coating which bonds to tissue of the PFO upon application of energy.

11. The device of claim 1, wherein the sleeve or coating comprises a material from the group consisting of a bioabsorbable material, a polymer, and a metal.

12. The device of claim 1, wherein the sleeve or coating comprises one or more substances for stimulating tissue growth.

13. The device of claim 1, wherein the occluding member comprises a spiral shaped device.

14. The device of claim 1, wherein the occluding member comprises nitinol or a bioabsorbable material.

15. The device of claim 1, wherein the plug further comprises a shape memory alloy.

16. The device of claim 15 wherein the shape memory alloy is nitinol.

\* \* \* \* \*